(12) United States Patent
Kirken et al.

(10) Patent No.: US 7,365,096 B2
(45) Date of Patent: Apr. 29, 2008

(54) METHODS FOR SELECTIVELY INHIBITING JANUS TYROSINE KINASE 3 (JAK3)

(75) Inventors: Robert A. Kirken, Conroe, TX (US); Barry D. Kahan, Houston, TX (US); Stanislaw M. Stepkowski, Pearland, TX (US); Waldemar Priebe, Houston, TX (US); Izabela Fokt, Spring, TX (US); Szymon Kosinski, Menomonee Falls, WI (US)

(73) Assignee: Board of Regents, The University of Texas System, Austin, TX (US)

( * ) Notice: Subject to any disclaimer, the term of this patent is extended or adjusted under 35 U.S.C. 154(b) by 300 days.

(21) Appl. No.: 10/731,769

(22) Filed: Dec. 9, 2003

(65) Prior Publication Data

US 2005/0203177 A1    Sep. 15, 2005

Related U.S. Application Data

(60) Provisional application No. 60/431,851, filed on Dec. 9, 2002.

(51) Int. Cl.
| | |
|---|---|
| A61K 31/21 | (2006.01) |
| A61K 31/13 | (2006.01) |
| A61K 31/12 | (2006.01) |
| A61K 8/73 | (2006.01) |

(52) U.S. Cl. .................. 514/513; 514/80; 514/690; 514/659; 424/49

(58) Field of Classification Search .................. 424/49; 514/80
See application file for complete search history.

(56) References Cited

U.S. PATENT DOCUMENTS

| | | | |
|---|---|---|---|
| 4,820,734 A | | 4/1989 | Bernauer et al. |
| 6,136,595 A | * | 10/2000 | Ihle et al. ............... 435/320.1 |
| 6,177,433 B1 | * | 1/2001 | Uckun et al. ............ 514/266.4 |
| 2002/0032204 A1 | | 3/2002 | Moon et al. |
| 2002/0042513 A1 | | 4/2002 | Uckun et al. |
| 2003/0013728 A1 | * | 1/2003 | Uckun ...................... 514/266.1 |

FOREIGN PATENT DOCUMENTS

| | | | | |
|---|---|---|---|---|
| CA | 712187 A | * | 6/1965 | |
| FR | 1466205 A | * | 4/1960 | |
| WO | 0242489 A1 | | 5/2002 | |

OTHER PUBLICATIONS

Database EMBASE on STN Online, No. 2003366614, Kahan et al. New Approaches of Transplant Immunosuppression, abstract, Transplantation Proceedings, 2003, 35/5, pp. 1621-1623.
Database EMBASE on STN Online, No. 2003391451, Manez, R. 'Current Trends in Transplantation and Immunosuppressive Treatment,' abstract, Drug News and Perspective, 2003, 16/5, pp. 332-336.
Database CAPLUS on STN Online, No. 1993:603032, Dimmock et al. Evaluation of Some Mannich Bases of Cycloalkanones and Related Compounds For Cytotoxic Activity, abstract, European Journal of Medicinal Chemistry, 1993, 28(4), pp. 313-322.
Database CAPLUS on STN Online, No. 1995:962281, Dimmock et al. 'Synthesis and Cytotoxic Evaluation of Some Mannich Bases of Alicyclic Ketones,' abstract, Pharmazie, 1995, 50(1), pp. 668-671.
Kane LP, Lin J, Weiss A. Signal transduction by the TCR for antigen. Curr Opin Immunol. (2000) 12:242-249.
Denton, MD, et al., Immunosuppressive strategies in transplantation. Lancet (1999) 353:1083-1091.
Mihatsch MJ, et al. The side effects of Ciclosporin-A and Tacrolimus. (1998) Clin. Nephrol 49 (6):356-363.
Kirken RA, Stepkowski SM. New directions in T-cell signal transduction and transplantation tolerance. Curr Opin in Organ Transplant (2002) 7:18-25.
Weiss A, Littman DR. Signal transduction by lymphocyte antigen receptors. Cell. (1994) 76:263-274.
Irving BA, et al. Functional characterization of a signal transducing motif present in the T cell antigen receptor zeta chain. J Exp Med. (1993) 177:1093-1103.
Chan AC, et al. ZAP-70 deficiency in an autosomal recessive form of severe combined immunodeficiency. Science. (1994) 264:1599-1601.
Appleby MW, et al. Defective T cell receptor signaling in mice lacking the thymic isoform of p59fyn. Cell. (1992) 70:751-763.
Kuo CT, Leiden JM. Transcriptional regulation of T lymphocyte development and function. Annu Rev Immunol. (1999) 17:149-187.
Leonard WJ, O'Shea JJ. JAKs and STATs: biological implications. Annu Rev Immunol. (1998);16:293-322.
Kondo M, et al. Sharing of the interleukin-2 (IL-2) receptor gamma chain between receptors for IL-2 and IL-4. Science. (1993) 262:1874-1877.
Noguchi M, et al. Interleukin-2 receptor gamma chain: a functional component of the interleukin-7 receptor. Science. (1993);262:1877-1880.
Russell SM, et al. Interaction of IL-2R beta and gamma c chains with Jak1 and Jak3: implications for XSCID and XCID. Science. (1994) 266:1042-1045.
Malabarba MG, et al. Interleukin-13 is a potent activator of JAK3 and STAT6 in cells expressing interleukin-2 receptor-gamma and interleukin-4 receptor-alpha. Biochem J. (1996) 319:865-872.
Szabo SJ, et al. Genes that regulate interleukin-4 expression in T cells, Curr Opin Immunol. (1997) 9:776-781.

(Continued)

Primary Examiner—Brian Kwon
(74) Attorney, Agent, or Firm—Conley Rose, P.C.

(57) ABSTRACT

Methods are disclosed for inhibiting or disrupting Janus tyrosine kinase 3 (Jak3) dependent function in cells of lymphoid or myeloid origin, especially for blocking proliferation and function of lymphocytes (e.g., T-cells, B-cells). A Mannich base compound, or a derivative or modified compound, is employed which is capable of selectively inhibiting Jak3 while affecting other protein tyrosine kinase activities to a lesser extent or not at all, to provide beneficial effects such as mitigation of transplant rejection and alleviation of allergic responses with fewer side effects than with conventional immunosuppressive agents.

40 Claims, 18 Drawing Sheets
(1 of 18 Drawing Sheet(s) Filed in Color)

OTHER PUBLICATIONS

Kirken RA, et al. Identification of Interluekin-2 Receptor-associated Tyrosine Kinase p116 as Novel Leukocyte-specific Janus Kinase. J Biol Chem (1994) 269(29):19136-19141.

Thomis TC, Berg LJ. Peripheral Expression of Jak3 Is Required to Maintain T Lymphocyte Function. J. Exp. Med. (1997) 185(2):197-206.

Kirken RA, et al. Tyrphostin AG-490 inhibits cytokine-mediated JAK3/STAT5a/b signal transduction and cellular proliferation of antigen-activated human T-cells. J Leukoc Biol (1999) 65:891-899.

Behbod F, et al. Concomitant inhibition of Janus kinase 3 and calcineurin-dependent signaling pathways synergistically prolongs the survival of rat heart allografts. J Immunol (2001) 166:3724-3732.

Stepkowski SM, et al. Selective inhibitor of Janus tyrosine kinase 3, PNU156804, prolongs allograft survival and acts synergistically with cyclosporine but additively with rapamycin. Blood (2002) 99:680-689.

Yamashita H, et al. Differential control of the phosphorylation state of proline-juxtaposed serine residues Ser725 of Stat5a and Ser730 of Stat5b in prolactin-sensitive cells. J Biol Chem. (1998) 273(46):30218-30224.

Kirken RA, et al. Activation of JAK3, but not JAK1, is critical for IL-2-induced proliferation and STAT5 recruitment by a COOH-terminal region of the IL-2 receptor beta-chain. Cytokine. (1995) 7(7):689-700.

Winters GL, et al. The international society for heart and lung transplantation grading system for heart transplant biopsy specimens: Clarification and commentary. J Heart Lung Transplant. 1998; 17:754-760.

Dimmock JR, Kumar P. Anticancer and Cytotoxic Properties of Mannich Bases. Current Medicinal Chemistry (1997) 4:1-22.

Dimmock JR, et al. Synthesis and Cytotoxic Evaluation of Some Mannich Bases of Alicyclic Ketones. Pharmazie (1995) 50:668-671.

Kirken RA. Targeting JAK3 for Immune Suppression and Allograft Acceptance. Transplantation Proc, (2001) 33:3268-3270.

Stepkowski, Stanislaw M. et al., "Selective Inhibitor Of Janus Tyrosine Kinase 3, PNU156804, Prolongs Allograft Survival And Acts Synergistically With Cyclosporine But Additively With Rapamycin," Blood, vol. 99, No. 2, Feb. 15, 2002, pp. 680-689.

Supplementary European Search Report for EP Application No. 03796805, Date of Completion Mar. 20, 2007, The Hague, 2 pgs.

* cited by examiner

| Treatment mg/kg/d | | | | |
|---|---|---|---|---|
| NC1153 | CsA | Ratio | MST ± SD | CI |
| 20 | 10 | 2:1 | 33.6 ± 10.04 | 0.30 |
| 40 | 5 | 8:1 | 28.8 ± 9.87 | 0.49 |
| 40 | 10 | 4:1 | 36.0 ± 10.05 | 0.36 |
| 80 | 5 | 16:1 | 36.6 ± 4.72 | 0.51 | all results displayed in mg/dL

* <0.05   • <0.01   † <0.001

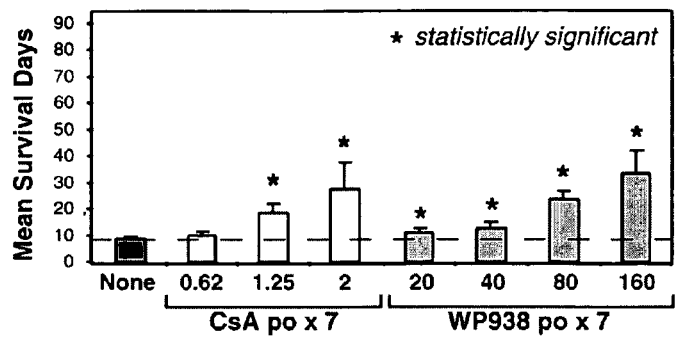
FIG. 12A
FIG. 12B
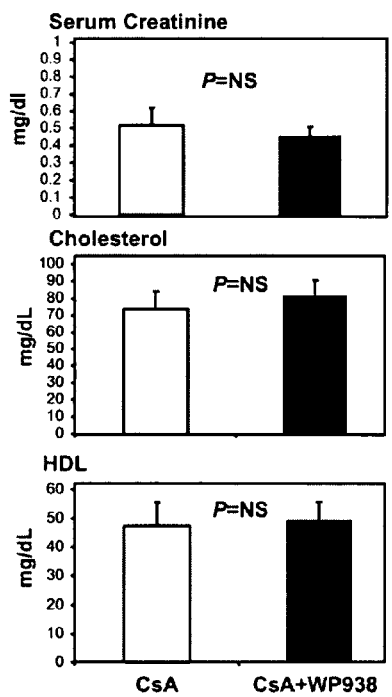
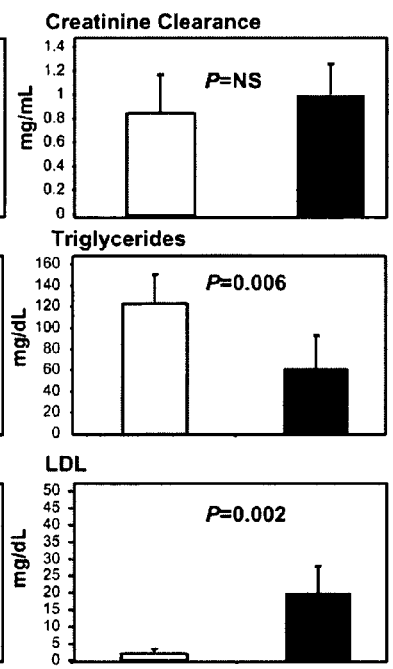
FIG. 13A
FIG. 13B
FIG. 13C
FIG. 13D
FIG. 13E
FIG. 13F FIG. 14A
FIG. 14B
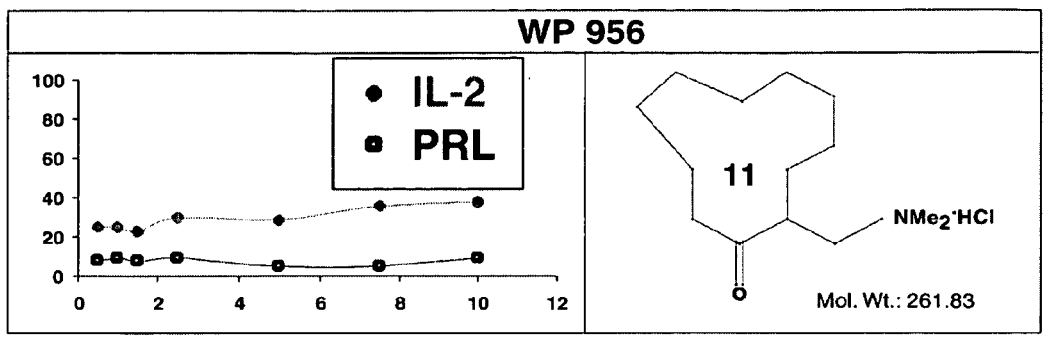
FIG. 15A
FIG. 15B
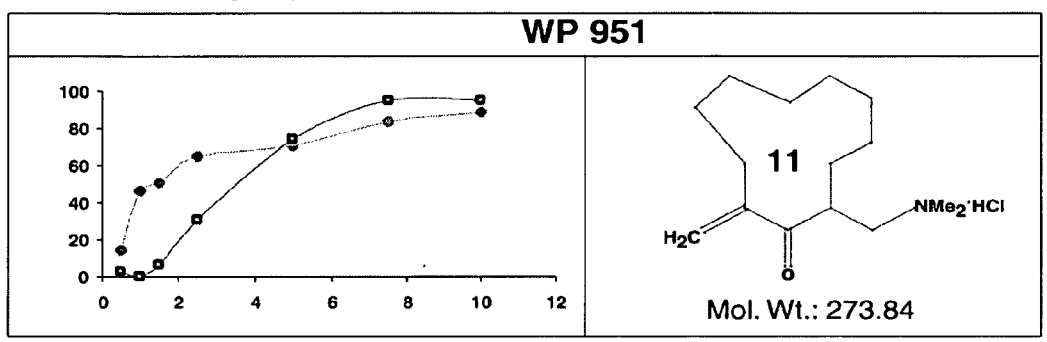
FIG. 16A
FIG. 16B
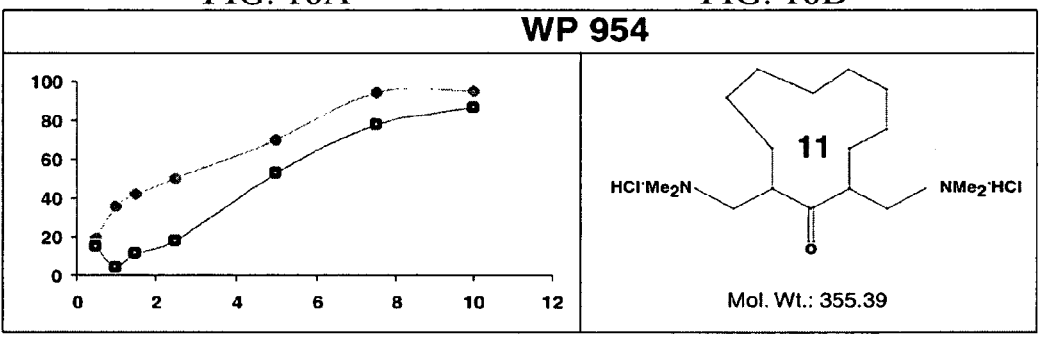
FIG. 17A
FIG. 17B
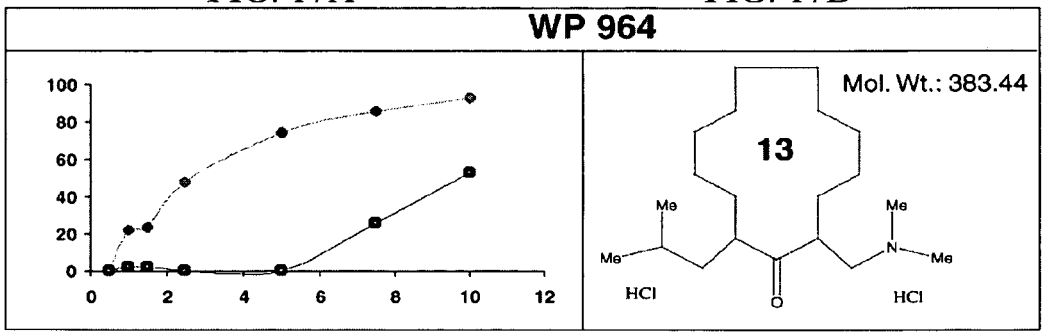

FIG. 26A  FIG. 26B
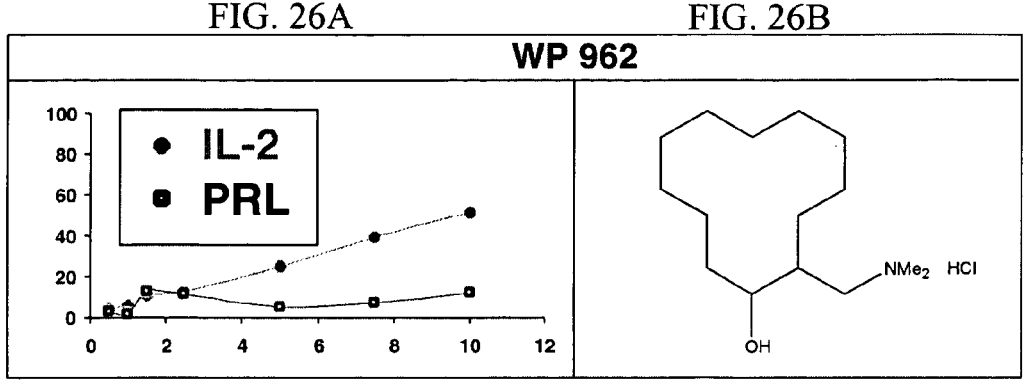
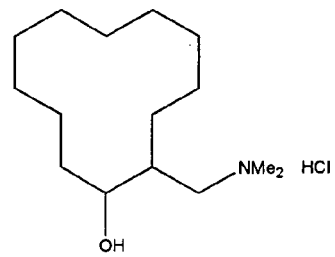
FIG. 27A  FIG. 27B
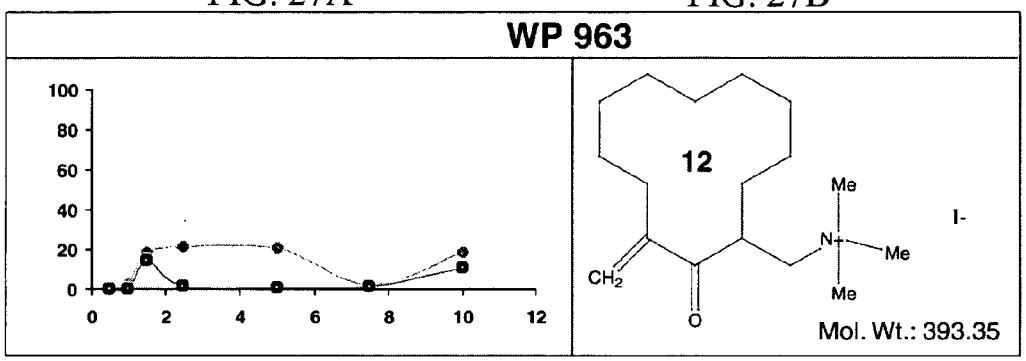
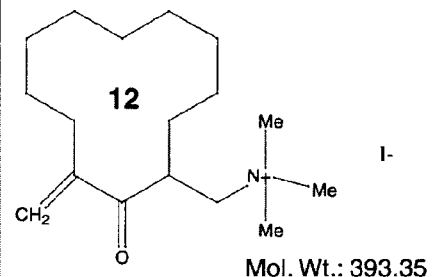
FIG. 28A  FIG. 28B
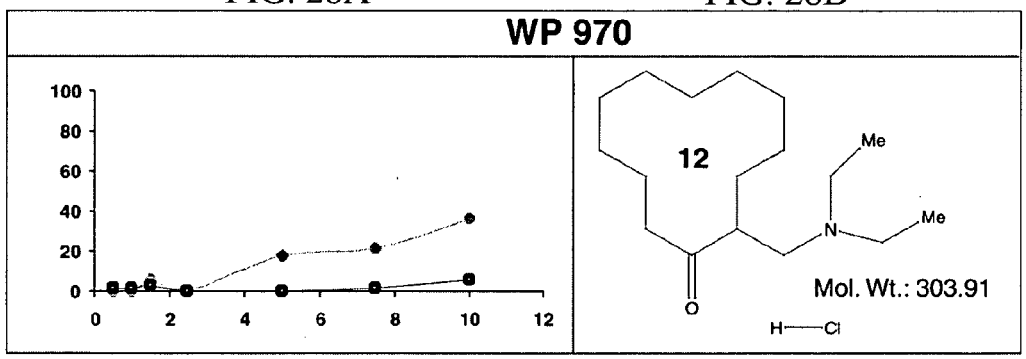
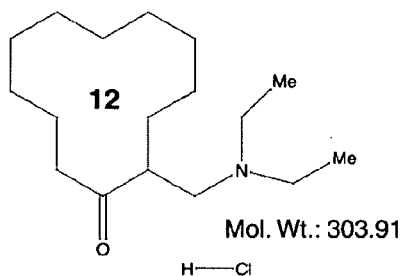
FIG. 29A  FIG. 29B
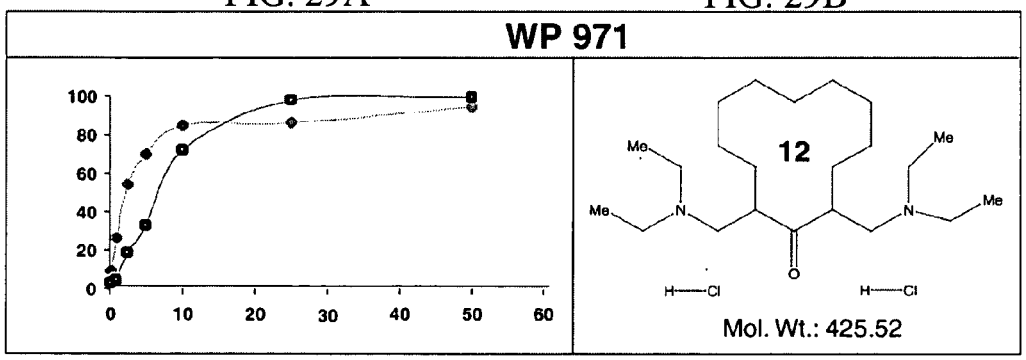
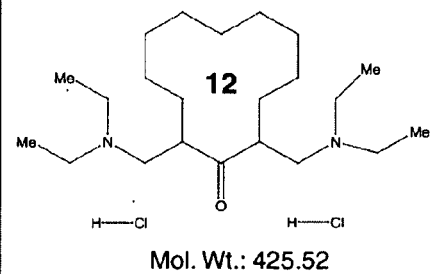

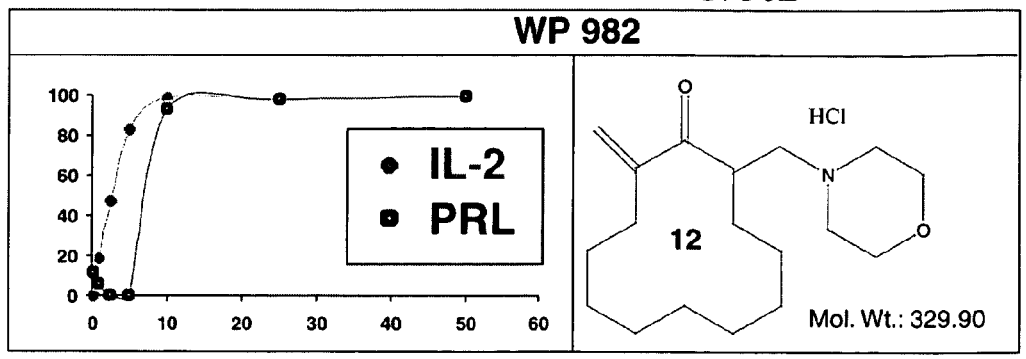
FIG. 30A / FIG. 30B — WP 982; Mol. Wt.: 329.90
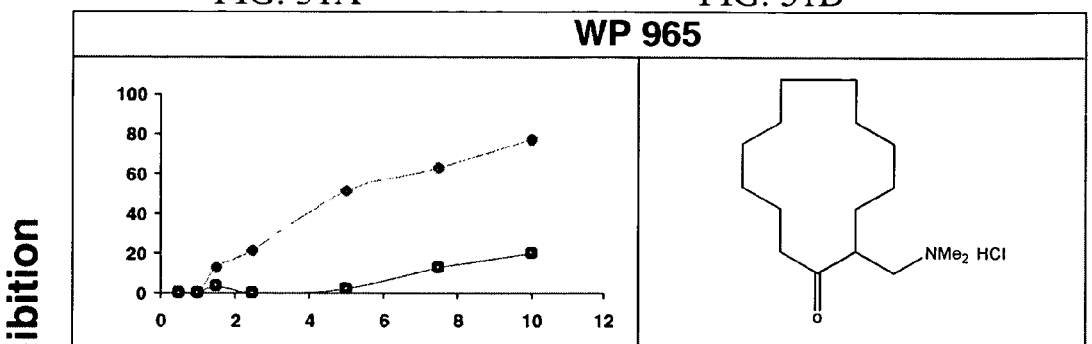
FIG. 31A / FIG. 31B — WP 965
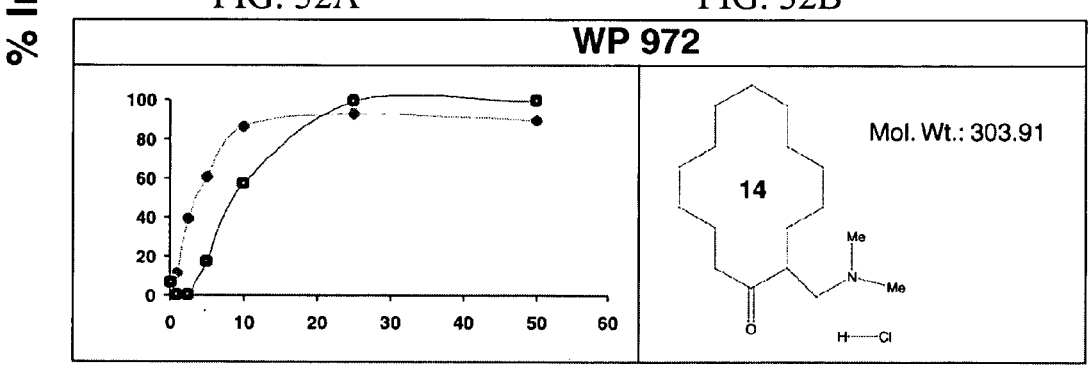
FIG. 32A / FIG. 32B — WP 972; Mol. Wt.: 303.91
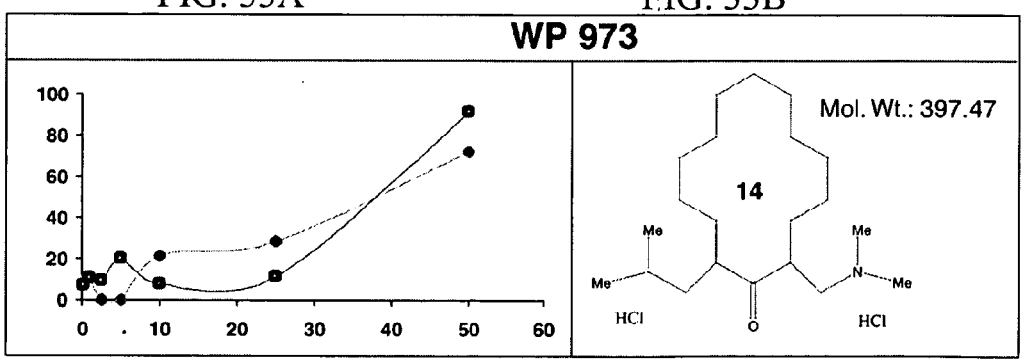
FIG. 33A / FIG. 33B — WP 973; Mol. Wt.: 397.47
Concentration [μm]

FIG. 38A
FIG. 38B
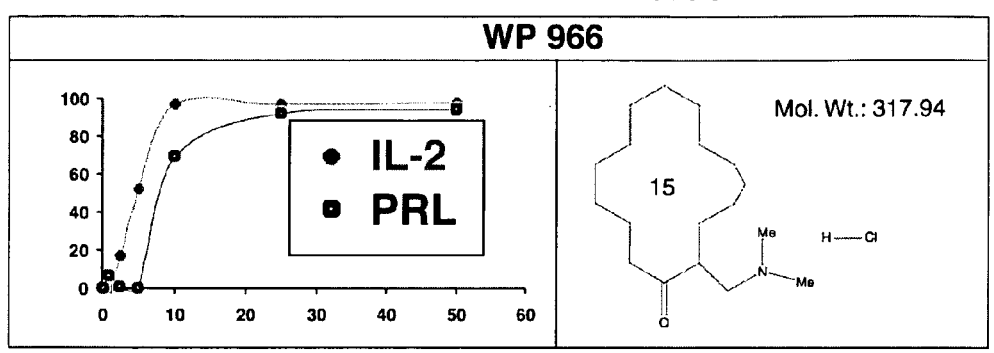
FIG. 39A
FIG. 39B
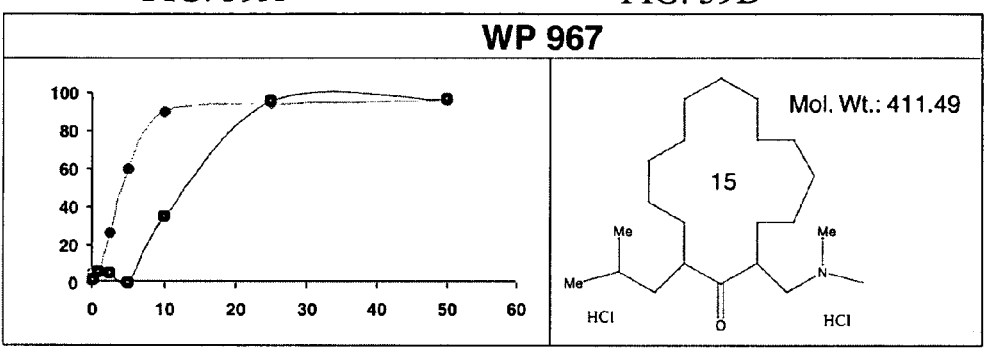

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: The promoter of the beta-casein gene.

<400> SEQUENCE: 1
agatttctag gaattcaatc c                                         21

<210> SEQ ID NO 2
<211> LENGTH: 21
<212> TYPE: DNA
<213> ORGANISM: Artificial
<220> FEATURE:
<223> OTHER INFORMATION: An NF-kB binding element.

<400> SEQUENCE: 2
agttgagggg actttccagg c                                         21

METHODS FOR SELECTIVELY INHIBITING JANUS TYROSINE KINASE 3 (JAK3)

CROSS-REFERENCE TO RELATED APPLICATIONS

This application claims the benefit under 35 U.S.C. § 119(e) of U.S. Provisional Patent Application No. 60/431,851 filed Dec. 9, 2002, the disclosure of which is hereby incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. N1DDK 38016-12 awarded by the National Institutes of Health.

BACKGROUND OF THE INVENTION

1. Field of the Invention

The present invention generally relates to inhibition of proliferation and function of lymphocytes and other cells of lymphoid origin which contain the Janus tyrosine kinase (Jak3). More particularly the invention relates to therapeutic and testing methods using chemical agents which block lymphocyte function, especially regulation of immune activity. Still more particularly, the invention relates to selectively disrupting Janus tyrosine kinase 3 (Jak3) mediated cell activities and cell proliferation.

2. Description of Related Art

The efficacy of therapeutic strategies in use today to combat organ allograft rejection is severely limited due to dependence on immunosuppressive drugs that produce potent side effects. Current clinical immunosuppressive regimens are dominated by the serine-threonine phosphatase calcineurin (CaN) inhibitors cyclosporin A (CsA) and tacrolimus (FK506),[1] which act as T-cell modifiers by blocking T-cell progression through the early $G_1$ stages of the cell cycle.[2] Undesirable side effects associated with those drugs include nephrotoxicity, neurotoxicity, diabetes mellitus, hyperlipidemia, hypertension, hirsutism, and gingival hyperplasia.[3] A newer drug, rapamycin (RAPA), which targets the serine-threonine kinase mammalian target of RAPA (mTOR), can also manifest mucosal ulcers, lymphoproliferative disorders, hypokalemia, and increases in low density lipoproteins, cholesterol, and triglycerides.[4] A serious drawback of the clinically approved drugs is that they do not yield permanent acceptance of allografts, and therefore they need to be continuously delivered to the patients.

Recent therapeutic strategies to combat organ allograft rejection have focused on T-cell signaling pathways and the molecules that comprise them. T-cell signaling cascades and their potential role in immunosuppression and potentially for the induction of transplantation tolerance are described by Kirken and Stepkowski.[5] Complete activation of T-cells requires three threshold-limited sequential signals.[6]

Signal 1 delivered by antigens that engage a specific T-cell receptor (TCR) is then followed by signal 2 delivered by a B7/CD28 interaction. Within seconds to minutes after TCR engagement, the CD3ζ chain is tyrosine (Tyr) phosphorylated during the autoactivation of Zap70, Lck, and Fyn protein Tyr kinases.[7-9] Concomitantly, calcium ($Ca^{2+}$) mobilization triggers catalytic activation of CaN phosphatase to dephosphorylate nuclear factor of activated T-cell (NFAT)—a necessary step for NFAT to translocate to the nucleus and bind discrete DNA binding elements within the promoter of the interleukin (IL)-2 gene.[10] Signals 1 and 2 are critical for the synthesis and secretion of IL-2, which, in concert with other T-cell growth factors (TCGFs) such as IL-4, -7, -9, -13, -15 and -21, deliver signal 3 through cytokine receptors, a necessary step required to drive clonal expansion of T-cells.[11] These cytokine receptors share a common γ chain ($\gamma_c$) that when combined with a unique α-chain for each cytokine deliver intracellular signals via Janus tyrosine (Tyr), Jak1 and Jak3, as well as activate signal transducers and activators of transcription (Stat)1, Stat3, Stat5a/b and Stat6.[11-18]

The CaN enzyme (participating in the signal 1 pathway in T-cells) and the mTOR enzyme (participating in the signal 3 pathway in T-cells) are ubiquitously expressed in various tissues throughout the body. This severely limits the efficacy of their inhibitory drugs such as CsA, FK506 and RAPA for T-cell specific targeting. RAPA is the only effective signal 3 inhibitor that has been clinically approved to date[24]. Unlike other signaling pathway molecules that serve as candidate targets for therapeutic intervention, Jak3 expression shows a limited pattern of tissue expression and is compartmentalized to T-cells, B-cells, natural killer (NK) cells and monocytes, or in general terms to cells of immune origin.

Due to its primary localization to lymphoid-type cells, Jak3 holds promise as a unique molecular and therapeutic target for ablating a number of immune-derived diseases.[19-21] This enzyme is almost exclusively associated and activated via $\gamma_c$, and therefore genetic disruption of Jak3 or $\gamma_c$ is manifested as severe combined immunodeficiency disease.[22] The reasons for this profound immune suppression is due to Jak3's critical role in T-cell development and recruitment by a family of TCGFs as mentioned above. Because Jak3 is associated with the receptor component and membrane proximal, all downstream signals emanating from these receptors, including Stat and mitogen activated protein kinase (Mapk) cascades would be activated. Thus, disruption of Jak3 subsequently blocks all signals mediated by TCGF and hence their ability to regulate gene transcription within these cells. However, if one could control the inhibition of this unique and redundant signaling pathway, favorable regulation of immune activity should be attainable as observed in patients and mice defective in these genes. Moreover, targeting this pathway would, in theory, also inhibit a population of activated and proliferating T-cells responsible for rejection that are not responsive to CsA[21].

Efforts to identify inhibitors that specifically target Jak3 in lymphocytes are hampered by the fact that the few reported drugs that inhibit Jak3 also inhibit a plethora of other tyrosine kinases that are required for routine cell function in many body tissues. Indeed these protein tyrosine kinases are fundamentally important for transducing extracellular signals from cell surface receptors to the nucleus, subsequently regulating growth, differentiation and function in cell types other than lymphocytes.

U.S. patent application Publication 2002/0042513 (Uckun et al.) describes certain quinazoline compounds that are selected on the basis of their estimated docking affinity using a Jak3 homology model based on structural homology to the insulin receptor tyrosine kinase. The ability of some quinazoline compounds to treat or prevent transplant complications, autoimmune induced diabetes, or to prolong allograft survival were evaluated.

U.S. patent application Publication No. 2002/0032204 (Moon et al.) describes certain Mannich base prodrugs of certain 3-(pyrrol-2-ylmethylidene)-2-indolinone derivatives that modulate the catalytic activity of receptor tyrosine kinases (RTKs), non-receptor protein tyrosine kinases (CTKs) and serine/threonine protein kinases (STKs). These prodrugs are said to be useful for treating many diseases mediated by abnormal protein kinase activity. The disclosed compounds are said to modulate RTK, CTK and/or STK mediated signal transduction pathways as a therapeutic approach to cure many kinds of solid tumors. Other Mannich base compounds have been described and evaluated for cytotoxicity and anticancer properties.[34,35] Certain Mannich bases of conjugated styryl ketones with antifungal and antineoplastic properties are the subject of U.S. Pat. No. 6,017,933.

Recently, two agents that show selectivity for Jak3 have been identified.[21,24,25] One agent denoted as AG-490 is a tyrphostin family member and a derivative of benzylidene malononitrile, which has the structural formula:

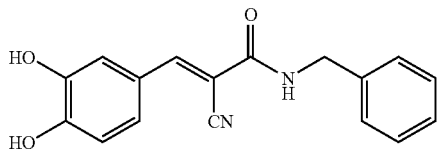

Another is PNU156804, which is a congener of the toxic parent compound undecylprodigiosin, and has the structural formula:

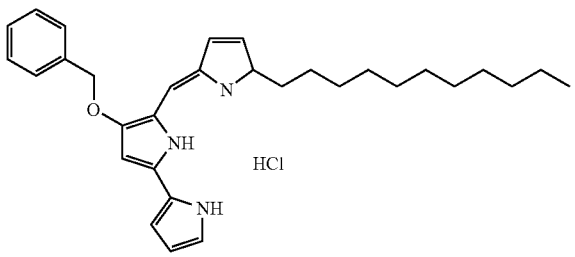

Both AG-490 and PNU156804 are competent to inhibit T-cell proliferation mediated by TCGFs and Jak3 autokinase activity, while having limited effects on unactivated T-cells that fail to express Jak3. It was found that neither of those two agents affects T-cell receptor activation cascade intermediates including p56Lck or Zap70 tyrosine kinases.[23,25]

In one study AG-490 treatment reduced graft infiltration of mononuclear cells (GICs) and Stat5a/b DNA binding of ex vivo IL-2 stimulated GICs, but failed to affect IL2Rα expression as judged by ribonuclease protection assays. Thus, it was concluded that inhibition of Jak3 prolongs allograft survival and also potentiates the immunosuppressive effects of CsA, but not RAPA. It was also found that AG-490 does not inhibit other tyrosine kinase family members Lck, Lyn, Btk, Syk, Src, Jak1 or Tyk2 kinases, while it does exert similar effects on its closest related family member Jak.[24] Adverse side effects of AG-490 preclude routine clinical use for immunosuppressive therapy.

PNU156804, on the other hand, displayed greater specificity by inhibiting Jak3 mediated T-cell growth by IL-2 as compared to other growth factors (prolactin) that use Jak2. Kinase assays showed that PNU156804 preferentially inhibited Jak3 autophosphorylation, as compared with Jak2, as well as shared intermediate effector molecules such as the Stat5 pathways.[25] In that study, it was shown that PNU156804 prolongs allograft survival and acts synergistically with CsA but additively with RAPA. It was also established that PNU156804 preferentially disrupts Jak3 (compared with Jak2 autokinase activity), thereby selectively inhibiting $\gamma_c$-driven T-cell clonal expansion. Current models hold that Jak3 is an upstream activator of mTOR. Since Jak3 is expressed in immune cells, inhibition of Jak3 will block mTOR activation without the adverse effects currently associated with RAPA. Moreover, synergy between CsA (blocking $G_0$-$G_1$ transition) and PNU156804 (blocking $G_1$-S progression) offers a novel strategy for immunosuppression by blocking sequential activation signals thereby requiring lower dosages of each drug while maintaining a beneficial therapeutic effect.[25] PNU156804 has subsequently proven to be too toxic for therapeutic use in humans, however.

While some currently available drugs have shown promise in blocking acute rejection, the problems of chronic graft destruction and permanent allograft acceptance (e.g. transplantation tolerance) in the absence of continuous immune suppression remain unabated. Therapeutic methods that adequately address these problems and pharmaceuticals that avoid adverse side effects are needed. Toward those goals, great strides have been made in understanding T-cell signal transduction and in devising strategies for targeting certain molecules in the signaling pathways. There is an urgent need for agents that selectively or specifically inhibit molecules unique for signal 3 pathways of T- and B-lymphocytes activated by TCGFs. Such agents have great potential for blocking clonal expansion of T-cells without affecting other cells. As discussed above, Jak3 represents a unique molecular target in the signal 3 pathway for regulating unwanted immune responses such as host-versus-graft and graft-versus-host disease.

SUMMARY OF PREFERRED EMBODIMENTS

The present invention seeks to overcome certain drawbacks inherent in the prior art by providing new ways to disrupt or inhibit function and/or proliferation of any cell type expressing Janus tyrosine kinase 3 (Jak3), preferably those of lymphoid or myeloid origin ("lymphoid or myeloid cells"), including T-cells, B-cells, natural killer (NK) cells, monocytes, macrophages and dendritic cells. Accordingly, in certain embodiments of the present invention, disruption or inhibition of lymphocyte function and/or proliferation is accomplished by treating the cell with certain compounds, preferably Mannich bases, to obtain therapeutic immunosuppression. In certain embodiments of the present invention, in vivo and in vitro therapeutic and testing methods are provided that employ certain Mannich base compounds, or other compounds, which were previously unknown or unrecognized as being capable of acting as immunosuppressive agents that preferentially disrupt Jak3 while leaving other widely disseminated protein tyrosine kinases virtually unaffected. When employed therapeutically, these agents also avoid entirely, or at least to some extent, the serious side effects commonly associated with conventional immunosuppressants in use today. Such methods are expected to be clinically useful in mitigating organ transplant rejection, in promoting the remission of autoimmune diseases, airway hypersensitivity (e.g. asthma), allergy, and in inhibiting proliferation of Jak3-dependent leukemia and lymphoma tumors, as well as other Jak3-dependent disorders in cells of lymphoid or myeloid origin which express Jak3.

Accordingly, in some embodiments of the present invention, an in vitro method of inhibiting lymphoid or myeloid cell proliferation and/or activity is provided in which the lymphoid or myeloid cell, such as a T lymphocyte, monocyte or a dendritic cell, comprises or expresses Jak3. The method comprises culturing the cells in the presence of a compound capable of selectively inhibiting Jak3. In some embodiments, a compound is employed, having formula (I)

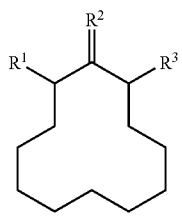

wherein $R_1$ is H, $=CH_2$, $CH_2N(CH_3)_2$, $CH_2SC(O)CH_3$, $CH_2SC_6H_5$, $CH_2SCH_2$-(4-$C_6H_4OCH_3$), $CH_2SC(O)C_6H_5$, or $CH_2N(CH_2CH_3)_2$; $R^2$ is O; and $R^3$ is $CH_2N(CH_3)_2$, $CH_2N(CH_2CH_3)_2$ and $CH_2$—(N-morphyl). In a preferred embodiment, the compound is 649641P (NC1153), having formula (I) wherein R1 and R3 are each $CH_2N(CH_3)_2$. In another preferred embodiment the compound is the meso stereoisomeric form of 649641P (NC1153), denoted as WP938.

In certain embodiments, a method of inhibiting lymphoid or myeloid cell function and/or proliferation is provided which comprises contacting a lymphoid or myeloid cell expressing Jak3 with at least one compound of formula (II)

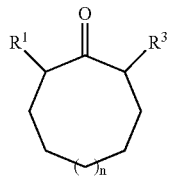

wherein n is 1, 2, 3, 4 or 6; $R_1$ is H, $=CH_2$, or $CH_2N(CH_3)_2$; and $R^3$ is $CH_2N(CH_3)_2$, or a salt of said compound, at a concentration effective to selectively inhibit the activity of said Jak3.

In certain embodiments, a method of inhibiting lymphoid or myeloid cell function and/or proliferation is provided which includes contacting a lymphoid or myeloid cell expressing Jak3 with at least one compound of formula (III)

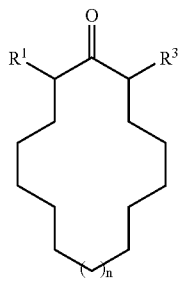

wherein n is 1 or 2; $R_1$ is H, or $CH_2N(CH_3)_2$; and $R^3$ is $CH_2N(CH_3)_2$, or a salt of said compound, at a concentration effective to selectively inhibit the activity of said Jak3.

In some embodiments of a method of inhibiting lymphoid cell function and/or proliferation, as described above, the lymphoid cell is an activated T-cell, and the method includes interfering with the signal 3 pathway such that cell division is blocked. In some embodiments, the lymphoid cell is contacted with the compound at a concentration effective to selectively inhibit Janus tyrosine kinase 3 and substantially ineffective to inhibit the activity of other protein tyrosine kinases. In some embodiments, Jak3 activity is inhibited in kinase assays at least 50 fold more than Jak2 activity in a population of lymphocytes, such as T-cells. In some embodiments, the method includes choosing one or more compound that is incapable or less capable of inhibiting Jak2 and Stat5a/b activation by prolactin (PRL) at a concentration sufficient to inhibit Jak3 and Stat5a/b activated by IL2.

In still other embodiments of the present invention, an in vitro testing method to aid in identifying substances that are useful as therapeutic immunosuppressants is provided. Such method may comprise: (a) obtaining a population of quiescent Jak3 dependent T lymphocytes in cell culture medium; (b) optionally, pretreating the quiescent T lymphocytes with a cytokine to stimulate the lymphocytes to proliferate; (c) treating the quiescent or stimulated lymphocytes from step (a) or (b) with any of the compounds, or their salts, having formula (I), (II) or (III), as set forth above; (d) culturing the lymphocytes from step (c) under cell growth promoting conditions; (e) assessing the extent of cell proliferation following step (d); (f) optionally, assessing the inhibitory effect of said compound on Jak2-dependent T lymphocyte proliferation; (g) optionally, assessing cytotoxicity of said compound; (h) determining from the assessments from step (e) and from (f) and (g), if present, that significant inhibition of Jak3-dependent lymphocyte, or other Jak3 expressing cell type, proliferation, not attributable to cytotoxicity of the compound, suggests that the compound has potential as a candidate drug for therapeutic use in vivo as a T-cell mediated immunosuppressant and/or as an inhibitor of T-cell proliferation; and (i) optionally, comparing the assessments from steps (e) and (f), and, if the inhibitory effects assessed in step (f) are significantly less than the inhibitory effects assessed in step (e), determining from said comparison that said compound is selective to at least some extent for inhibiting Jak3 activity compared to inhibiting Jak2 activity, or another kinase.

In accordance with another embodiment of the present invention, an in vivo method of suppressing an undesired function of a cell in a mammalian subject is provided, wherein the cell comprises Jak3. The method includes contacting the cell with at least one of the compounds having formula (I), (II) or (III) as set forth above, or a metabolite or derivative thereof, in an amount effective to interfere with the signal 3 pathway in the cell and thereby inhibit cell function. The contacting comprises administering to the subject a therapeutically effective amount of a pharmaceutical composition containing at least one such compound, or mature form of the compound such as an active metabolite, or a precursor of said compound capable of being converted in the body of the subject to said compound, or a pharmaceutically acceptable salt of any of those, in a pharmaceutically acceptable carrier, to inhibit Jak3-dependent cell function. The administering may be carried out continuously or periodically. In some embodiments the Jak3-containing cell is a T-cell and the amount of the pharmaceutical composition administered is effective to block cell division in the T-cell. In certain preferred embodiments the nephrotoxicity of the compound, metabolite, derivative, or precursor is less than that of cyclosporin A.

In accordance with certain embodiments of the present invention, is provided a method of therapeutically treating a mammalian subject to suppress an undesired immune response, wherein the subject is experiencing or is at risk of experiencing an undesired immune response. This method includes carrying out an above-described method of suppressing an undesired lymphocyte function in a mammalian subject wherein the therapeutically effective amount of the pharmaceutical composition mitigates or prevents said undesired immune response. In certain embodiments, the method further includes administering to the subject a therapeutically effective amount of an immunosuppressive agent other than a Jak3 inhibitor; for example, cyclosporin A or FK506. This offers the advantage of inhibiting T-cell function by blocking T-cell activation via the signal 1 pathway and also by blocking cell division of the activated T-cell via interfering with the signal 3 pathway.

In accordance with certain embodiments of the present invention, a method of mitigating organ transplant rejection in a mammalian transplant recipient is provided which comprises carrying out an above-described method of suppressing an undesired lymphocyte function in a mammalian subject effective to suppress a T-cell mediated immune response to the transplanted organ whereby rejection of the organ is mitigated or arrested.

In accordance with certain embodiments of the present invention, a method of mitigating acute allograft rejection in a mammalian allograft recipient is provided which includes carrying out an above-described method of suppressing an undesired lymphocyte function in a mammalian subject effective to suppress a T-cell mediated anti-allograft immune response whereby acute rejection of the allograft is mitigated or prevented. In some embodiments, a method for prophylaxis of chronic allograft rejection is provided which includes continuous or periodic administration of the Jak3 inhibitor composition.

In accordance with certain embodiments of the present invention, a method is provided for inducing transplantation tolerance in a mammalian transplant recipient. The method includes carrying out an above-described method of suppressing an undesired lymphocyte function in a mammalian subject effective to suppress a T-cell mediated transplant rejection response.

In accordance with certain embodiments of the present invention, a method of promoting remission of an autoimmune disease in a mammalian subject suffering from said disease is provided. The method comprises carrying out an above-described method of suppressing an undesired lymphocyte function in a mammalian subject effective to suppress a T-cell mediated autoimmune response in said subject whereby autoimmune attack on the subject's native tissue mediated by endogenous Jak3-dependent T-cells is diminished or arrested.

In accordance with certain embodiments of the present invention, a method of mitigating airway hypersensitivity in a mammalian subject suffering from said hypersensitivity is provided. The method includes carrying out an above-described method of suppressing an undesired lymphocyte function in a mammalian subject effective to suppress a T-cell mediated hypersensitivity response in the subject whereby hypersensitivity of airway tissue in the subject is diminished or arrested.

Some embodiments of the present invention provide a method of mitigating allergy in a mammalian subject suffering from said allergy which includes carrying out an above-described method of suppressing an undesired lymphocyte function in a mammalian subject effective to suppress a T-cell mediated allergic response in the subject whereby an allergic reaction in the subject is diminished or arrested.

Still other embodiments of the present invention provide a method of inhibiting proliferation of a Jak3-dependent leukemia or lymphoma which comprises carrying out an above-described method of suppressing an undesired lymphocyte function in a mammalian subject suffering from leukemia or lymphoma. In preferred embodiments, the compound or its metabolite or derivative is capable of selectively or specifically inhibiting Jak3 activity compared to inhibition of the activity of other kinases (e.g., Jak2). The amount of the pharmaceutical composition is effective to inhibit or block proliferation of leukemia or lymphoma cells.

In additional embodiments of the present invention, in vitro methods are provided which are useful for elucidating the biological processes associated with T-cell mediated immune responses and for identifying new immunosuppressive drugs. In some embodiments, an in vitro method to aid in identifying a new immunosuppressive drug is provided which comprises (a) testing a compound of interest for activity for disrupting T-cell function by contacting a T-cell comprising Jak3 with a compound of interest over a range of concentrations and determining whether the compound inhibits Jak3 activity at one or more concentration within the range; (b) comparing the Jak3 inhibitory activity of the compound of interest to that of a compound of formula (I), (II) or (III) having known Jak3 inhibitory activity, preferably 649641P (NC1153); and (c) using the results of such testing and comparing to determine whether the compound of interest is a candidate drug for in vivo use as a therapeutic immunosuppressive agent. In some embodiments the method also includes (d) testing the compound of interest for inhibitory activity of one or more other kinase (e.g., Jak2); (e) comparing the Jak3 inhibitory activity of the compound of interest to its inhibitory activity, if any, of one or more other kinase; and (f) using the comparisons to identify the compound of interest as a selective Jak3 inhibitor.

In another embodiment of the present invention, in vivo testing methods are provided which employ certain Jak3 selective or specific inhibitors. Such methods will be useful for studying T-cell mediated immune responses in animal models, and compounds such as 649641P (NC1153), WP938, and others identified in FIGS. 14B-39B may serve as a standard for comparing the activity of candidate Jak3 specific inhibitors. One such method for testing a candidate immunosuppressive drug for its effect on allograft survival includes: (a) implanting an allograft taken from a suitable donor animal into a suitable recipient animal; (b) maintaining basic nutrition and health promoting conditions for the animals; (c) administering the candidate drug to each of at least one animal, to provide a treated recipient or group; (d) administering to at least one animal the compound as defined in claim 1, wherein $R^1$ and $R^3$ are each $CN(CH_3)_2$ and $R^2$ is), to serve as a positive control group; (e) optionally, leaving at least one recipient animal untreated, to serve as an untreated control recipient or group; (f) determining allograft survival time of each allograft in each recipient; (g) performing histological examination of each allograft and assessing candidate drug related structural damage to each allograft, as applicable; (h) comparing the allograft survival time and the candidate drug induced histological structural changes in each allograft; and (i) using the comparisons from (h), determining that enhanced graft survival time and lack of drug induced structural damage to the drug treated allografts compared to the allograft(s) from the untreated control recipient(s) or compared to the allograft(s) from the positive control recipient(s) is indicative that the candidate drug is likely to be effective when used therapeutically in vivo as an immunosuppressive agent. In some embodiments, the method also includes determining that the candidate drug is capable of selectively inhibiting Jak3 dependent T-cell proliferation in vitro.

In certain other embodiments, in vivo methods of evaluating a candidate drug for in vivo immunosuppressive potential are provided. The candidate drug is preferably first identified as being capable of selectively inhibiting Jak3 dependent T-cell proliferation in vitro. The method includes (a) implanting an allograft taken from a suitable donor animal into a suitable recipient animal; (b) maintaining basic nutrition and health promoting conditions for the animals; (c) administering the candidate drug to each of at least one animal, to provide a treated recipient or group; (d) administering 649641P (NC1153) to each of at least one animal, to serve as a standard recipient or group; (e) preferably, leaving at least one recipient animal untreated, to serve as an untreated control recipient or group; (f) determining allograft survival time of each the allograft in each recipient; (g) performing histological examination of each the allograft and assessing drug related structural damage to each allograft, as applicable; and (h) comparing the allograft survival time and the drug induced histological structural changes in each allograft; and (i) using the comparisons from (h), determining that enhanced graft survival time and lack of drug induced structural damage to the drug treated allografts compared to the allograft(s) from the untreated control recipient(s) or compared to the allograft(s) from the positive control recipient(s) is indicative that the candidate drug is likely to be effective when used therapeutically in vivo as an immunosuppressive agent. These and other embodiments, features and advantages of the present invention will become apparent with reference to the following description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows IL-2 activated Jak3 tyrosine phosphorylation in human YT cells.

FIG. 2B shows the effect of 649641P (NC1153) on IL-2 activated Stat5a tyrosine phosphorylation in human YT cells. FIG. 2C shows the effect of 649641P (NC1153) on IL-2 activated Stat5b tyrosine phosphorylation in YT cells.

FIG. 6A is 649461P (NC1153). FIG. 6B is RAPA.

FIG. 6C is CsA. FIG. 6D is shows the combined effects of CsA and RAPA (sirolimus or SRL). FIG. 6E shows the combined effects of CsA and 649641P (NC1153).

FIG. 7A is a bar graph showing that proliferation of PHA-activated human T cells was blocked by the indicated NCI agents following stimulation with IL-2. FIG. 7B is a FACS analysis of PHA-activated T-cell blasts that were treated without (heavy line) or with 50 µM NC1153 (light line) overnight and stained for IL2R-α, -β, and -γchains. FIG. 7C is a graph of cell growth inhibition over a range of NC1153 concentration in non-Jak3 expressing Jurkat cells (black diamonds) and in Jak3 containing PHA activated T-cells (open boxes). FIG. 7D is a graph of cell growth inhibition versus NC1153 concentration in T-cells stimulated by cytokines that utilize Jak3 and the common gamma chain.

FIG. 9A is an electrophoretic mobility shift assay (EMSA) autoradiograph showing that 649641P (NC1153) inhibits Jak3 driven transcription factor-Stat5a/b in PHA activated T-cells treated with increasing concentrations of 649641P (NC1153) in a dose dependent manner (upper panel). Non-Jak3 mediated NfκB activation by TNF-α was not affected within the same treatment set (lower panel). FIG. 9B is a Western blot autoradiograph demonstrating that 649641P (NC1153) fails to inhibit closely related Jak2/Stat5a signaling pathway. Prolactin [PRL] (+) or (−) indicates whether the cells were stimulated with prolactin with Jak2 activation. Phosphotyrosine Western blots detect Jak2-Stat5 activation but no inhibition by 649641P (NC1153). FIG. 9C is a bar graph demonstrating that 649641P (NC1153) fails to affect the activity of multiple kinases other than Jak3. 649641P (NC1153) was tested at 10 (open bars) or 50 µM (filled bars) to block growth factor tyrosine kinases (FGFR3 and PDGFRα), Src family tyrosine kinases (Src, Fyn, Lck, Yes, Zap70) or serine threonine kinases (PKC and PKA) phosphorylation of a substrate. The activity of the control is plotted as a dashed line.

FIG. 10A shows graft survival in ACI rat recipients of Lewis (LEW) kidney allografts treated for 7 days with 649641P (NC1153) delivered by daily i.v. injections (left panel) or by oral gavage (right panel). FIG. 10B shows graft survival in similar recipients treated for 14 days with 649641P (NC1153) delivered by daily oral gavage. FIG. 10C shows graft survival in similar recipients treated for 7 days and thereafter 3×/week up to 90 days with 160 mg/kg NC1153 delivered by daily oral gavage. FIG. 10D demonstrates the synergistic effect of NC1153 delivered by daily oral gavage with CsA in ACI rat recipients of LEW kidney allografts treated for 7 days. 649641P (NC1153)

alone (dark bars). CsA alone (open bars). 649641P (NC1153) and CsA (light bars).

Figure 11A:
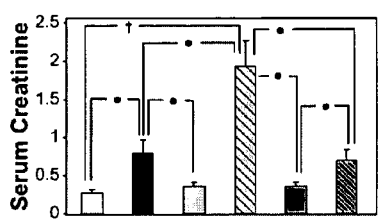
Figure 11B:
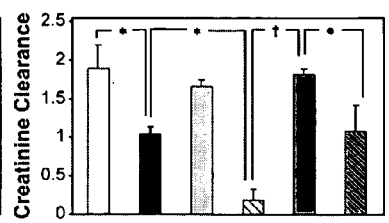
Figure 11C:
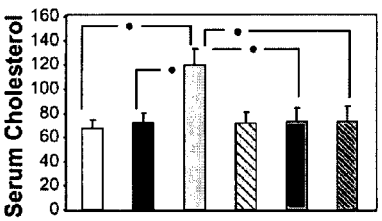
Figure 11D:
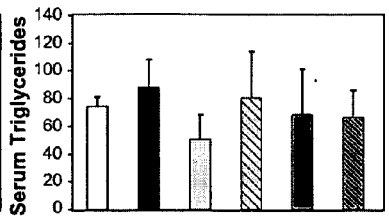
Figure 11E:
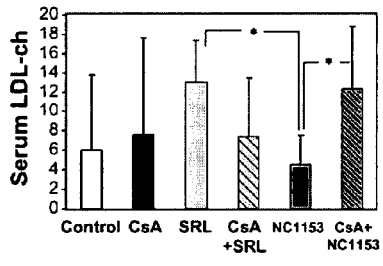
Figure 11F:
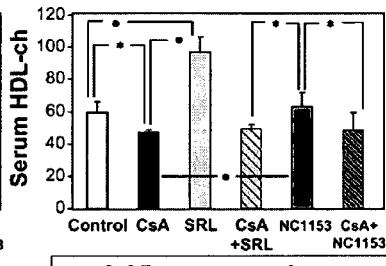

FIGS. 11A-F are graphs of assay results demonstrating that 649641P (NC1153) is not nephrotoxic and does not affect lipid metabolism, evaluated by serum creatinine levels (FIG. 11A) serum creatinine clearance (FIG. 11B), serum cholesterol (FIG. 11C), triglycerides (FIG. 11D), LDL-cholesterol (FIG. 11E), and HDL-cholesterol (FIG. 11F). Results are displayed in mg/dL. Histological appearance was as shown in FIGS. 6A-E.

Figures 18A, 18B:
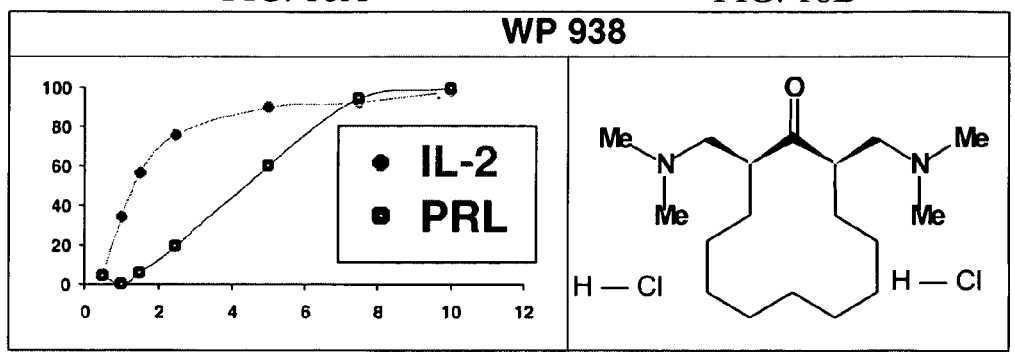
Figures 19A, 19B:
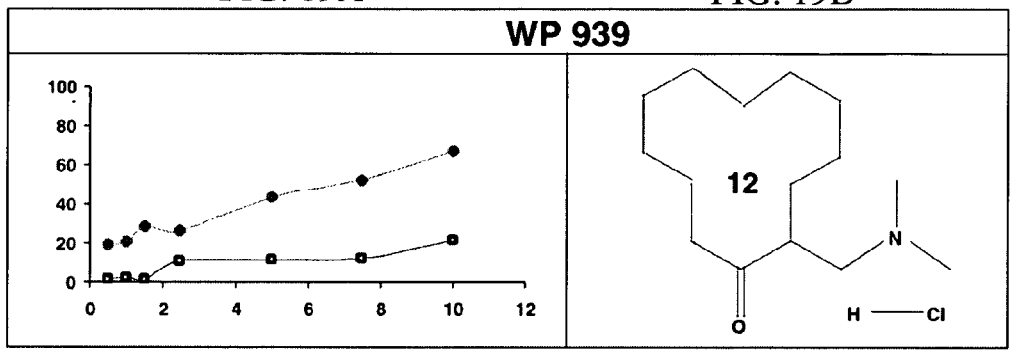
Figures 20A, 20B:
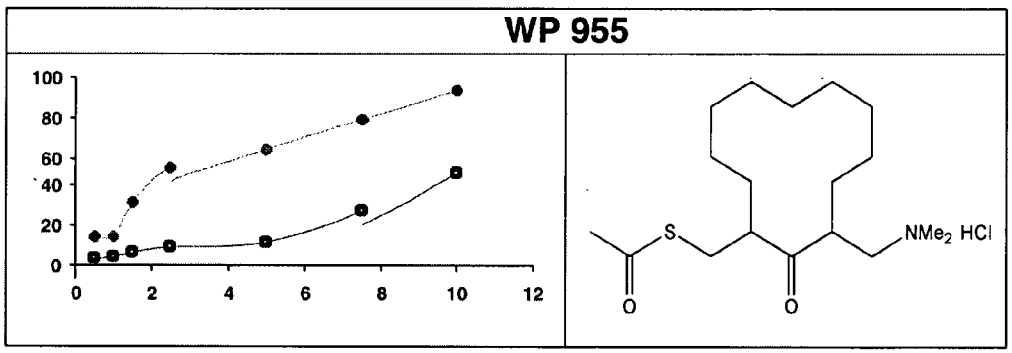

FIGS. 12A-B are analogous to FIGS. 10A-D, except that they show the results with the meso stereoisomer of 649641P (NC1153) designated WP938 (shown in FIG. 18B) that was tested for allograft survival in ACI recipients of LEW kidney allografts. FIG. 12A shows mean survival of untreated, CsA alone treated, and WP938 alone treated rats. FIG. 12B shows comparison of one dose CsA alone, one dose WP938 alone in comparison with the same doses of CsA/WP938 combination; CI value of 0.44 documents synergistic interaction.

FIGS. 13A-F show the results of toxicity assays for WP938 alone or in combination with CsA. FIG. 13A indicates serum creatine levels. FIG. 13B indicates creatinine clearance. FIG. 13C indicates cholesterol levels. FIG. 13D indicates triglyceride. FIG. 13E indicates HDL levels. FIG. 13F indicates LDL levels.

FIGS. 14A,B-39A,B show the chemical formulas of a number of compounds and their activities for inhibiting Jak3-dependent or Jak-3 independent proliferation of T-cells in an in vitro assay. (A) IL-2 stimulated (light circles); PRL stimulated (dark circles). (B) The corresponding structural formula of each compound (shown as a salt).

DETAILED DESCRIPTION OF PREFERRED EMBODIMENTS

In studies described herein it is confirmed that a biochemical intermediate—the enzyme Janus tyrosine kinase 3 (Jak3)—is critical for mature T-cell activation, function and allograft rejection. Certain compounds identified herein, especially those classified as Mannich bases, which selectively inhibit Jak3, may offer therapeutic advantages over conventional immunosuppressive drugs such as CsA, FK506, and RAPA. As discussed in the background section above, RAPA inhibits mTOR, whereas CsA and FK506 blocks CaN, and both of those target molecules display ubiquitous expression profiles causing potent toxic side effects. In contrast, Jak3 expression is confined exclusively to the lymphoid compartment, including T and B lymphocytes.

Figures 21A, 21B:
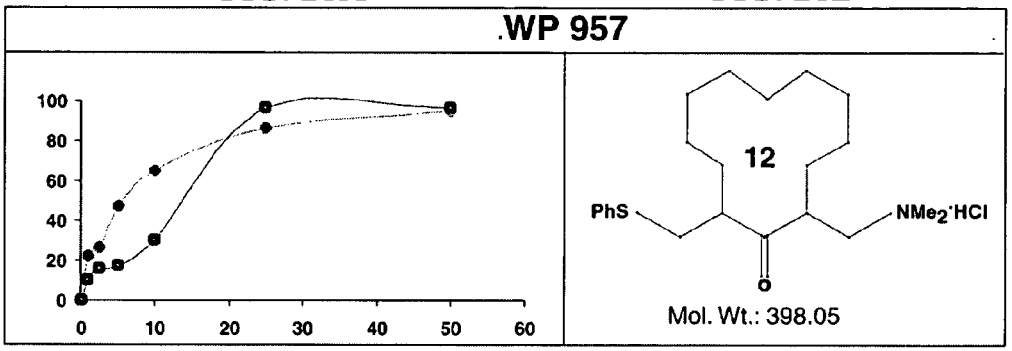
Figures 22A, 22B:
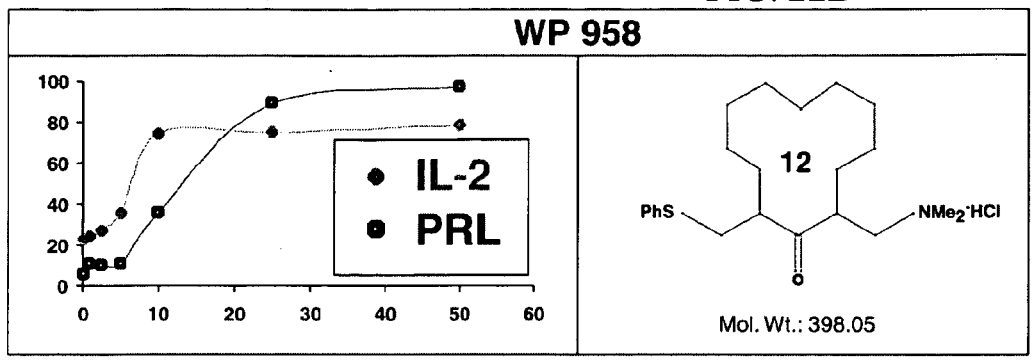
Figures 23A, 23B:
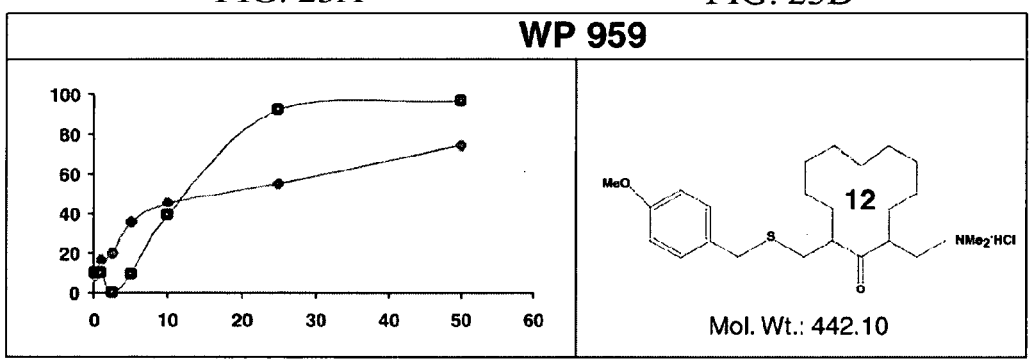
Figures 24A, 24B:
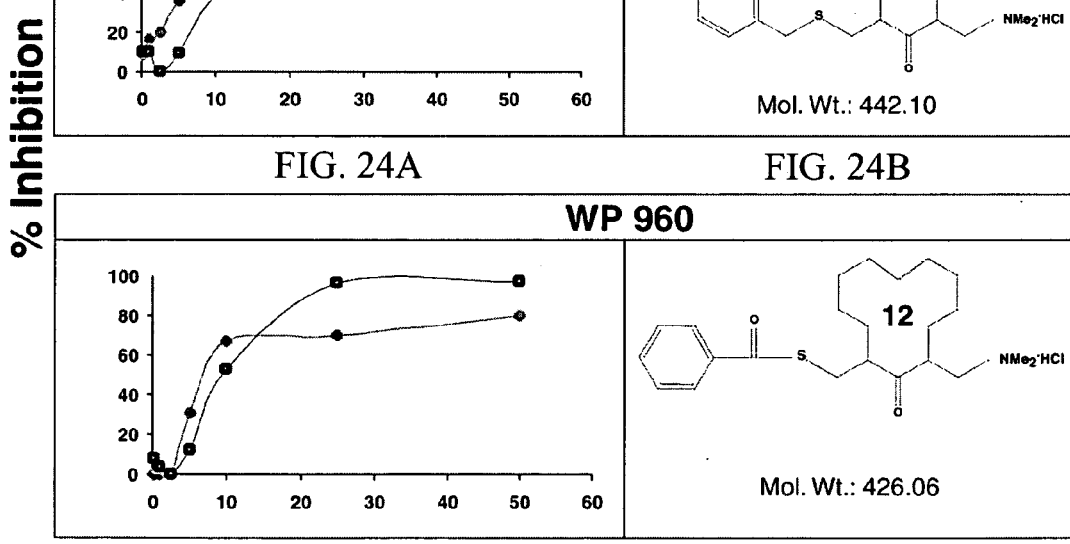
Figures 25A, 25B:
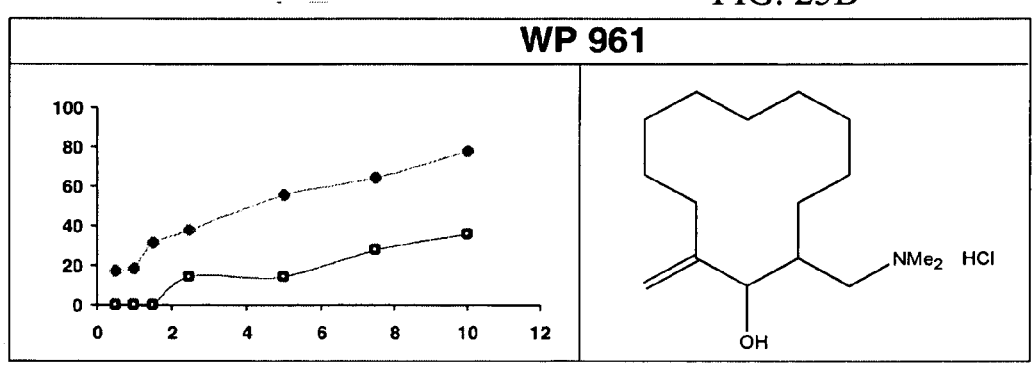
Figures 34A, 34B:
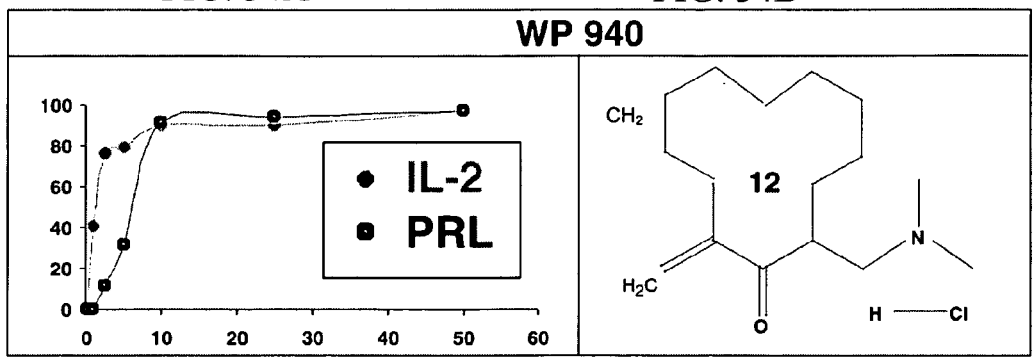
Figures 35A, 35B:
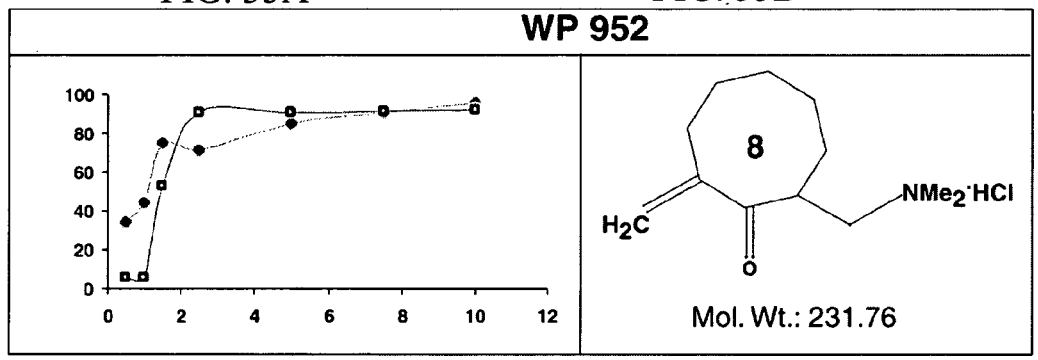
Figures 36A, 36B:
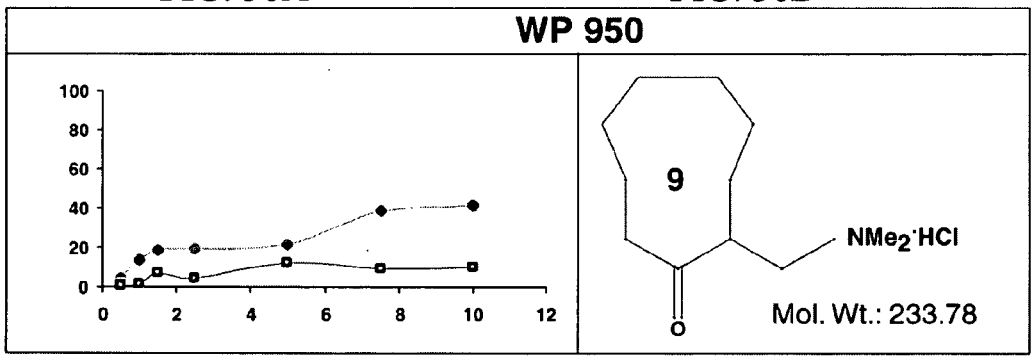
Figures 37A, 37B:
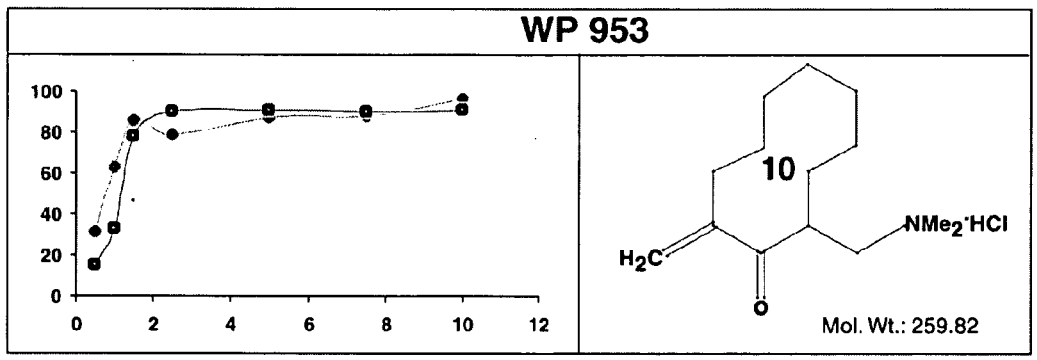

Initially, a series of tests were performed seeking to identify and characterize antagonists of Jak3, which thereby inhibit an entire family of TCGF-dependent pathways. A group of Mannich-base and other compounds, were screened for selective Jak3 inhibitory activity over a range of concentrations. Those which demonstrated some measure of selective inhibition of IL-2 stimulated (i.e., Jak3-dependent) T-cell proliferation, compared to prolactin (PRL) stimulated (i.e., Jak2-dependent) T-cell proliferation, along with some structurally similar compounds, are shown by their structural formulas in FIGS. 14B-39B. The corresponding inhibitory activity of each compound is shown in FIGS. 14A-39A. FIG. 22A shows the results of assays similar to those of FIG. 21A, but with a slightly different purity preparation of the same compound as FIG. 21B. In addition to Mannich bases, structurally similar compounds (FIGS. 25B and 26B) are included among the compounds tested.

The following materials and general methods were used, except as otherwise stated in the Examples. A representative compound, 649641P, also referred to herein by its NCI drug database number NC1153, and a meso stereoisomer shown in FIG. 18B (denoted WP938), which demonstrated identical selective Jak3 inhibition in vitro, were tested further for ability to prolong allograft survival alone or in combination with CsA, as well as for drug-induced toxicities.

General Methods and Materials

Cell culture and treatment. The rat T-cell line Nb2-11c, originally developed by Dr. Peter Gout (Vancouver, Canada), was grown in RPMI-1640 with 10% fetal calf serum (Intergen, cat. no. 1020-90), 2 mM L-glutamine, 5 mM HEPES, pH 7.3, and penicillin-streptomycin (50 IU/ml and 50 µg/ml, respectively), at 37° C./5% $CO_2$. Freshly explanted normal human T lymphocytes purified by isocentrifugation (Ficoll®; EM Science, Gibbstown, N.J.) were phytohemagglutinin (PHA)-activated for 72 hours as previously described.[23] T lymphocytes were made quiescent by washing and incubating for 24 hours in RPMI-1640 medium containing 1% fetal calf serum before exposure to cytokines. Next, cells were treated with varying concentrations of 649641P (NC1153) as described below in the figure descriptions. The Mannich base 649641P (NC1153) was generously provided by Dr. Jonathan Dimmock College of Pharmacy, University of Saskatchewan, Saskatoon, Saskatchewan, Canada. All cells were then stimulated with 1 nM recombinant human IL-2 (Hoffman-LaRoche, Basel, Switzerland), IL4 or IL7 (PeproTech), or ovine prolactin (PRL) supplied by the National Hormone and Pituitary Program, National Institute of Diabetes, Digestive, and Kidney Disease (Bethesda, Md.), at 37° C. Cell pellets were frozen at −70° C.

Proliferation assays. Quiescent human primary T-cells, YT or rat Nb2-11c T-cells ($5.0 \times 10^4$/well) were plated in flat-bottom, 96-well microtiter plates in 200 µl of quiescent media in the absence or presence of 1 nM IL-2, -4, -7 (PeproTech, Rock Hill, N.J.), or PRL. Next, cells were treated for 16 hours with the Mannich base drug and then pulsed for 4 hours with [$^3$H]-thymidine (0.5 µCi/200 µl) and harvested onto fiberglass filters. [$^3$H]-thymidine incorporation was analyzed by liquid scintillation counting as previously described,[23] or using standard techniques that are well known in the art.

Solubilization of membrane proteins, immunoprecipitation, and Western blot analysis. Frozen cell pellets were thawed on ice and solubilized in 1% TX-100 lysis buffer ($10^8$ cells/ml) and clarified by centrifugation, as previously described.[16] For human T-cells, supernates were incubated rotating end over end for 2 hours at 4° C. with either 5 µl/ml polyclonal rabbit antisera raised against peptides derived from the unique COOH-termini of Jak3 (amino acid [a.a.] 1104-1124), carboxyl termini of human Stat5a (a.a. 775-794) or Stat5b (a.a. 777-787).[26] Ab and immunoprecipitated proteins were captured by incubation for 30 minutes with Protein A-Sepharose beads (Pharmacia, Piscataway, N.J.), sedimented for purification, and eluted by boiling in 2×SDS-sample buffer (20% Glycerol, 10% 2-Mercaptoethanol, 4.6% SDS, 0.004% Bromophenol blue in 0.125 M Tris pH 6.8) for 4 minutes. For phosphoMapk assays, approximately 25 µg of total cell lysate was dissociated in SDS-sample buffer and separated on 10% (all others on 7.5%) SDS-PAGE under reducing conditions. Proteins were transferred to polyvinylidene difluoride (Immobilon™; cat. no. 1PVH 00010, Millipore, Bedford, Mass.) as previously described.[27] Western blot analysis was performed with either pAbs, murine anti-phosphotyrosine monoclonal antibodies (mAbs;

UBI; 4G10; cat. no. 05-321, Upstate Biotechnology, Inc., Lake Placid, N.Y.), or phospho p44/42 Mapk (New England Biolabs, Beverly, Mass., Cat no. 9101). Blots Westerned with the above antibodies, rabbit antiphospho-Erk1/2, and monoclonal pan-Erk (Pharmingen, San Diego, Calif., Cat no. E17120) were diluted 1:1000 in blocking buffer and used as previously described,[27] or employing standard techniques that are well known in the art. Blots Westerned with rabbit antiphospho-tyrosine (αPY), and monoclonal mouse anti-Fyn or anti-Lck antibodies (BD Biosciences, San Diego, Calif., Cat no. 610163 [Fyn] and 610097 [Lck]) were diluted 1:1000 in blocking buffer as previously described[27].

Rat Kidney Transplants. Adult male ACI (RT1$^a$) and Lewis (LEW; RT1$^1$) rats (160-200 g) obtained from Harlan Sprague-Dawley (Indianapolis, Ind.) were cared for according to the guidelines of the Animal Welfare Committee. Rats were housed in light- and temperature-controlled quarters and given chow and water ad libitum. Kidneys were transplanted heterotopically from LEW donors to ACI recipients using a standard microsurgical technique of Ono and Lindsey[28]. For immunosuppressive drug evaluation, transplant recipients were treated with the Mannich base compound by daily intravenous (i.v.) injection or oral gavage (p.o.), alone or in combination with CsA or RAPA administered daily by oral gavage. A control group of recipients remained untreated. Some recipients were treated with CsA or RAPA alone. Graft survival time was defined as animal survival of life supporting kidney transplant. The results, presented as mean survival time (MST)±standard deviation (SD), were assessed for statistical significance by Gehan's survival test. In addition, the interaction between the Mannich base and CsA or RAPA was evaluated by the median effect analysis.[29,30] Computer software was used to calculate combination index (CI) values: CI<1 showed synergistic, CI>1 antagonistic, or CI=1 additive interactions.[30]

Histopathologic Evaluation. ACI (RT1$^a$) recipients of LEW (RT1$^1$) kidney allografts kidney allografts were treated as described in the Examples which follow. At day 7 posttransplant, kidney allografts were placed in Bouin's Fixative (Poly Scientific R&D Corp., Bay Shore, N.Y.). Each kidney was sectioned in an identical fashion consisting of single horizontal cut followed by three consecutive incisions used to generate slides. Next, another dissection was made followed by three more consecutive slices and slides generated. A total number of 12 slides per kidney were stained with hematoxylin-eosin (H&E) as described previously,[31] or using standard techniques that are known in the art. The degree of rejection was graded in accordance with the standards established by Society of Heart and Lung Transplantation.[32] In particular, kidneys were fixed in buffered 10% formalin and processed overnight; 3-μ histologic sections were stained with progressive hematoxylin-eosin (H&E) reagents. Two independent pathologists used semi-quantitative scales of light microscopic criteria to assess the degree of vasculopathy, glomerular changes, and tubulo-interstitial damage in multiple kidney sections. Tubular and glomerular changes were separately graded as 0=no changes; 1+=<5%; 2+=5-25%; 3+=26-50%; and 4+=>50% involvement. A similar vascular scale included 0=None; 1+=minimal; 2+=mild; 3+=moderate; and 4+=severe.

EMSA. Electrophoretic mobility shift assay (EMSA). Drug or vehicle control (DMSO) treated cells were pelleted by centrifugation (20,000×g for 1 min at 4° C.) and subsequently washed in five volumes of 10 mM HEPES, pH 7.9, 10 mM KCl, 1.5 mM MgCl$_2$, 0.5 mM DTT, 100 mM PMSF, 5 μg/ml aprotinin, 1 μg/ml pepstatin A and 2 μg/ml leupeptin, centrifuged, then lysed in the same buffer supplemented with 1% NP-40 and incubated for 20 min on ice. The nuclei-containing pellet was resuspended in equal volumes of low salt buffer (10 mM HEPES, 25% glycerol, 1.5 mM MgCl$_2$, 20 mM KCl, 0.5 mM DTT, 0.2 mM EDTA and protease inhibitors) and high salt buffer (low salt buffer containing 800 mM KCl). This fraction was then isolated by centrifugation at 4° C. for 10 min and supernatants saved as nuclear protein extract and stored at −70° C. Gel mobility shift assays were performed to detect Stat5a/b DNA binding activity using a Stat5 DNA binding sequence corresponding to the promoter of the β-casein gene (5'-AGATTTCTAG-GAATTCAATCC-3') or an NF-kB binding element (5'-AGTTGAGGGGACTTTCCAGGC-3'). Both probes were end-labeled with [$^{32}$P]dATP. Labeled-oligonucleotides were then incubated with 5 μg of nuclear extracted proteins in 15 μl of binding cocktail (50 mM Tris-Cl, pH 7.4, 25 mM MgCl$_2$, 5 mM DTT, 50% glycerol) at 4° C. for 2 h. For supershift assays, nuclear extracts were pre-incubated with 1 μg of either normal rabbit serum or antisera specific to Stat5a, Stat5b, or p50/p65 NFκB (Santa Cruz Biotechnology, Inc., Santa Cruz, Calif.; Cat no. sc-1190X and sc-372X, respectively) as indicated in legend at 4° C. for 1 h then incubated with [$^{32}$P]-labeled DNA oligonucleotide for 15 min at room temperature. The DNA-protein complexes were resolved on 5% polyacrylamide gels containing 0.25×TBE which were pre-run in 0.25×TBE buffer for 1 hour at 100 V. Samples were loaded and gels were run at room temperature for approximately 2 h at 150 V then dried by heating under vacuum and exposed to X-ray film (X-Omat, Kodak) at −70° C.

Mannich Bases and Other Compounds. The compound 649641P (NC1153) used in initial investigations was provided by Dr. Jonathan R. Dimmock of the University of Saskatchewan, Saskatoon, Canada. 649641P (NC1153) and other compounds, including those identified in FIGS. 14B-39B, were prepared by Dr. Waldemar Priebe of the M.D. Anderson Cancer Center, University of Texas System, Houston, Tex. The compounds described herein may be prepared by any suitable methods using commercially available starting materials and reagents available from suppliers such as Aldrich Chemical Co., (Milwaukee, Wis.) and Sigma (St. Louis, Mo.). Standard chemical synthesis techniques and procedures may be employed, as set forth in references such as Fieser and Fieser's REAGENTS FOR ORGANIC SYNTHESIS, Volumes 1-17 (John Wiley and Sons, 1991); Rodd's CHEMISTRY OF CARBON COMPOUNDS, Volumes 1-5 and Supplementals (Elsevier Science Publishers, 1989); ORGANIC REACTIONS, Volumes 1-40 (John Wiley and Sons, 1991), March's ADVANCED ORGANIC CHEMISTRY, (John Wiley and Sons, 4th Edition) and Larock's COMPREHENSIVE ORGANIC TRANSFORMATIONS (VCH Publishers Inc., 1989). Additional guidance for synthesizing the compounds can be found in the periodical literature, for example, the publications of Dimmock[34,35], and as set forth below.

The following non-limiting examples are illustrations of the characteristics and uses of a representative Jak3-selective inhibitor compound and are not meant to limit the invention in any way.

EXAMPLE 1

In Vitro Effects of Mannich Base 649641P (NC1153)

The Mannich base denoted 649641P ($C_{18}H_{38}C_{12}N_2O$; MW 369.41), also referred to as NC1153, as a mixture of its stereoisomers, and having the general formula

Figure 1A:
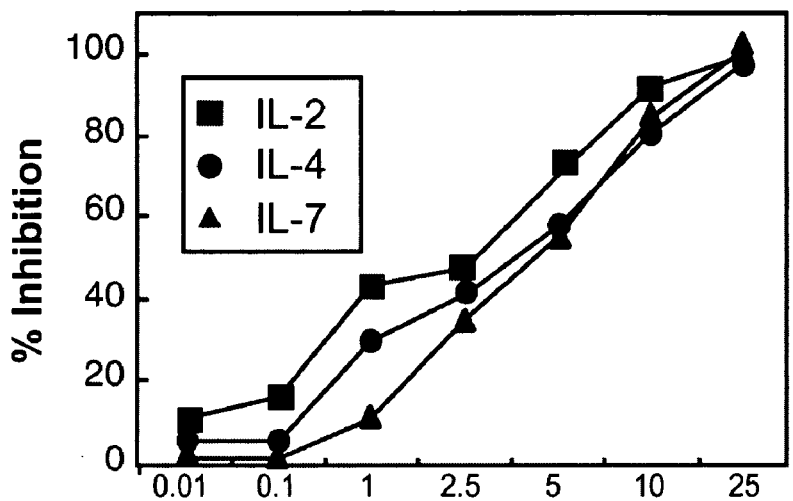
FIG. 1A is a graph showing the dose-dependent effect of 649641P (NC1153) on γc/Jak3-dependent PHA-activated human T cell proliferation cultured in the absence or presence of 1 nM human IL-2 (■), IL-4 (•), or IL-7 (▲) normalized to untreated controls.

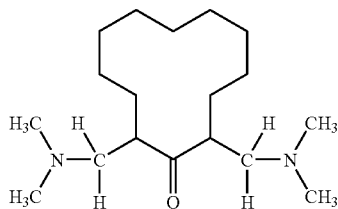

was added to T-cells undergoing Jak3-versus Jak2-dependent proliferation, as described above, to test its ability to selectively inhibit Jak3. FIG. 1A is a graph showing the effect of 649641P (NC1153) on proliferation of γc/Jak3-dependent PHA-activated human T-cells. Quiescent PHA-activated human T-cells ($5.0 \times 10^4$ cells/well) were cultured in the absence or presence of 1 nM human IL-2 (■), IL-4 (•), or IL-7 (▲) with increasing concentrations of 649641P (NC1153) (ordinate) for 16 hours at 37° C. Cells were then pulsed with [$^3$H]-thymidine (0.5 μCi/200 μl) for 4 hours and incorporated radiolabeled probe plotted on the abscissa expressed as % inhibition of total cpm from DMSO-treated sample sets (n=6).

Figure 1B:
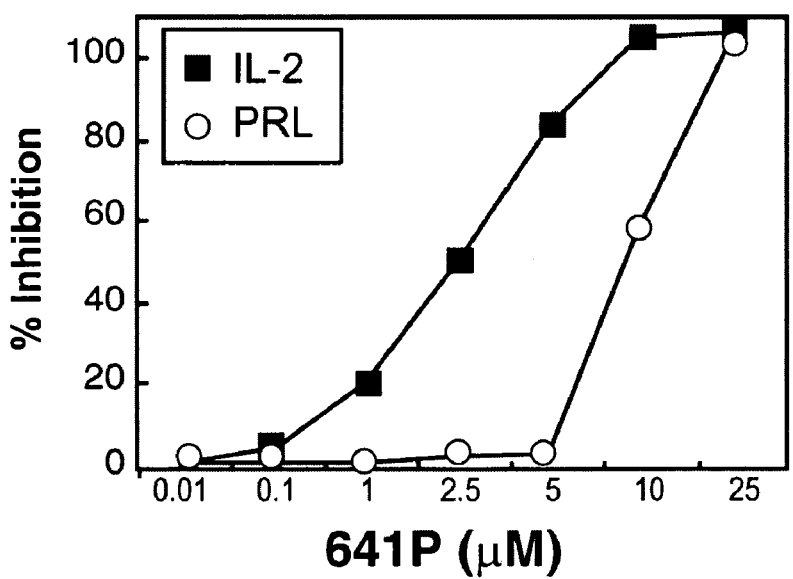
FIG. 1B is a graph showing the inhibitory effect of 649641P (NC1153) on Jak2 versus Jak3 dependent rat T cell proliferation when cultured in the presence of the Jak2 activator (PRL[○]) or the Jak3 activator (IL-2 [■]).

FIG. 1B shows the effect of 649641P (NC1153) on proliferation of T-cells cultured in the presence of the Jak2 activator (prolactin; PRL [○]) or the Jak3 activator (interleukin-2; IL-2 [■]). The rat T cell line (Nb2-11c) was chosen because it responds to either PRL/Jak2 or IL-2/Jak3 stimulation. Quiescent rat T cells ($5.0 \times 10^4$ cells/well) were cultured in the presence of the Jak2 activator (1 nM PRL ([○]) or Jak3 activator (1 nM IL-2 [■]), with increasing concentrations of 649641P (NC1153) (ordinate; 0-100 μM) for 16 hours at 37° C. Cells were pulsed with [$^3$H]-thymidine (0.5 μCi/200 μl) during the final 4 hours of the assay then the DNA-incorporated radiolabeled probe was plotted on the abscissa and expressed as % inhibition of total cpm from DMSO-treated sample sets (n=4). As shown in FIGS. 1A-B, 649641P (NC1153) selectively inhibits γc/Jak3-dependent but not PRL/Jak2-dependent cell proliferation. In particular, although 649641P (NC1153) proved to be equally effective to inhibit Nb2-11c cell proliferation in response to IL-2, IL-4 and IL-7, the same compound was 3-fold more effective for inhibiting Jak3- than Jak2-dependent proliferation.

Figure 2A:
FIGS. 2A-2C are Western blots showing inhibition or no inhibition by 649641P (NC1153) on phosphorylation.
Figure 2B:
Figure 2C:
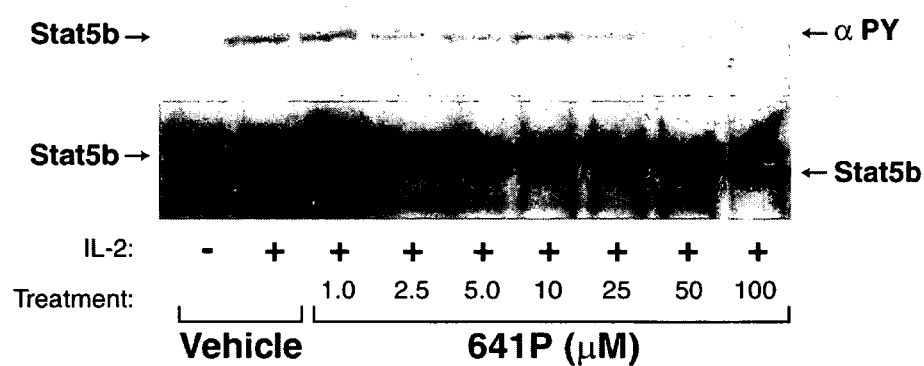

In FIGS. 2A-C the effect of 649641P (NC1153) on the Jak3/Stat5 signal pathway is shown. Human YT cells were cultured without (a-b) or with (c-i) ascending concentrations (1-100 μM) of 649641P (NC1153) for 2 hours and re-challenged for 10 minutes with (+) or without (−) 100 nM IL-2. Cells were immunoprecipitated with anti-Jak3 pAb and Western blotted with anti-phosphotyrosine mAb, as shown in FIG. 2A, upper panel, and then stripped and re-blotted with anti-Jak3 (FIG. 2A, lower panel). These Western blot experimental results, in which tyrosine phosphorylation of Jak3 was inhibited in a dose-dependent fashion by 649641P (NC1153) in human YT cells (1-100 μM), correlate with those shown in FIG. 1A. Referring now to FIG. 2B, human YT T-cells were also cultured without (a and b) or with (c through i) ascending concentrations (1-100 μM) 649641P (NC1153) for 2 hrs and re-challenged for 10 minutes with (+) or without (−)100 nM IL-2. Cells were immunoprecipitated with anti-Stat5a pAb and Western blotted with anti-phosphotyrosine mAb (FIG. 2B, upper panel) and then stripped and re-blotted with Stat5a (FIG. 2B, lower panel). In a third test, the results of which are shown in FIG. 2C, human YT cells were cultured without (a-b) or with (c-i) ascending concentrations (1-100 μM) 649641P (NC1153) for 16 hrs and re-challenged for 10 minutes with (+) or without (−)100 nM IL-2. Cells were immunoprecipitated with anti-Stat5b pAb and Western blotted with anti-phosphotyrosine mAb (FIG. 2C, upper panel) and then stripped and re-blotted with anti-Stat5b (FIG. 2C, lower panel).

Figure 3:
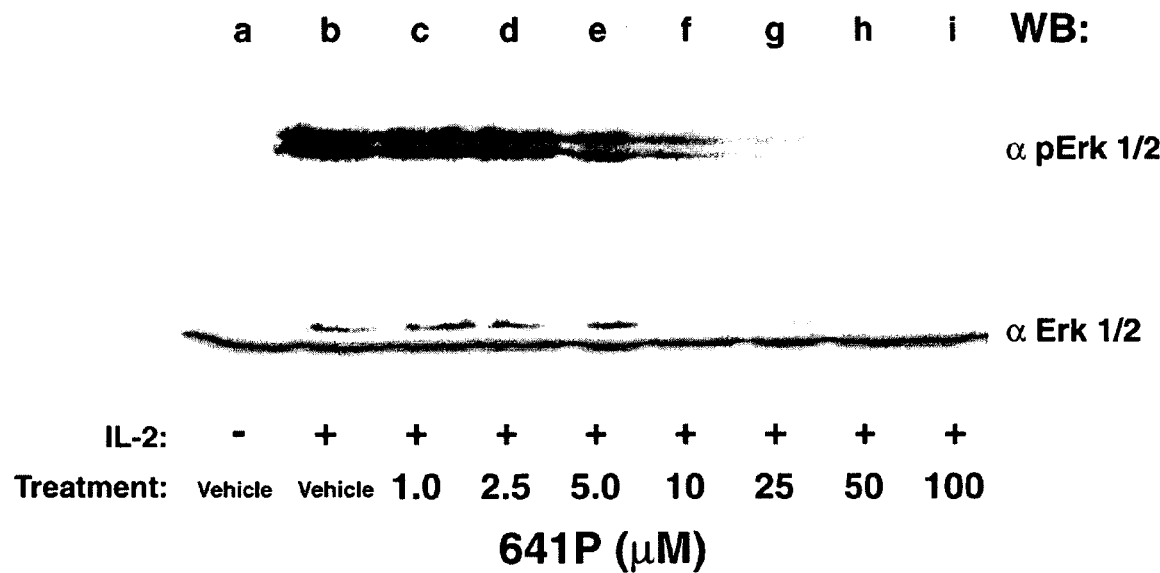
FIG. 3 is a Western blot showing the effect of 649641P (NC1153) on IL-2-activated p44/42 ERK1/2 phosphorylation in PHA-activated T-cells.

IL-2 also potently activates the Shc/Ras/Raf/Erk pathway via the adapter protein, Shc, which binds to Tyr338 of the IL-2Rβ chain ultimately to drive T-cell proliferation. FIG. 3 shows the results of a similar experiment to those described above in which the effect of ascending 649641P (NC1153) concentrations on IL-2-mediated p44/42 Erk1/2 phosphorylation was investigated. Quiescent PHA-activated T cells were treated with DMSO (control; lanes a-b) or increasing concentrations (c-i) of 649641P (NC1153) for 2 hours and then stimulated in the presence of 1 μg at 37° C. for 10 minutes. Cells were lysed and total cell lysate separated on 10% SDS-PAGE, transferred to PVDF membrane Western blotted with anti-phospho-p44/42 Erk1/2 (upper panel), then stripped and reprobed with pan Erk antibody (lower panel). Arrows indicate location of p44/42 Erk1/2. These results reveal that 649641P (NC1153) blocks IL2-mediated Erk1/2 activation in human T-cells.

Figure 4:
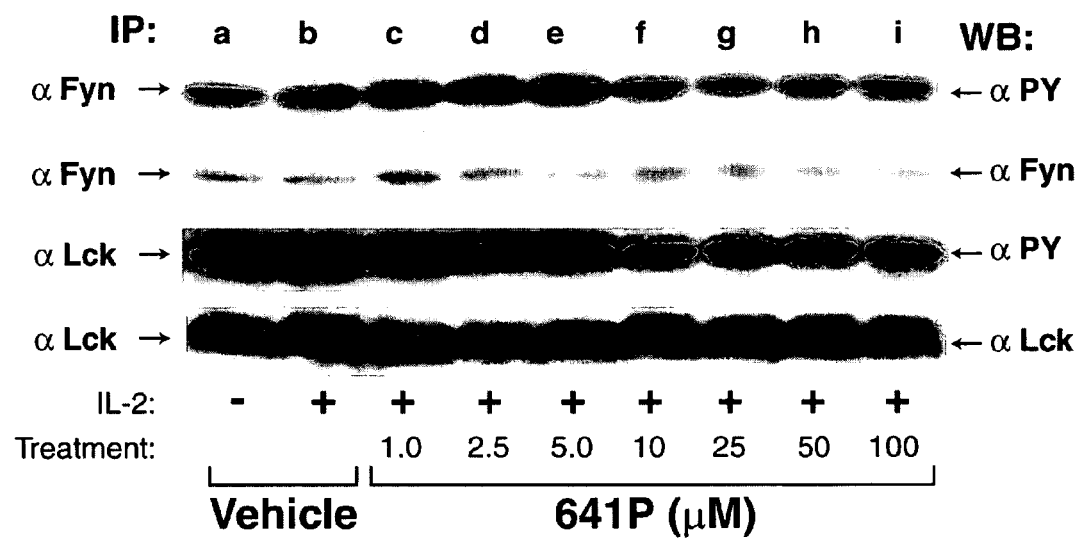
FIG. 4 is a Western blot showing no effect of 649641P (NC1153) on activated Fyn and Lck in YT cells.

YT cells constitutively express activated Fyn and Lck kinases that can be shown by testing for their tyrosine phosphorylation status. YT cells were cultured for 2 hours with different concentrations of 649641P (NC1153) (1-100 μM). Cellular extracts were immunoprecipitated with anti-Fyn or anti-Lck antibodies and Western blotted with anti-phosphotyrosine antibodies (αPY), then stripped and re-blotted with anti-Fyn or anti-Lck antibodies. FIG. 4 shows the results of above described experiment: YT cell extracts immunoprecipitated with anti-Fyn and Western blotted with anti-phosphotyrosine antibodies (αPY) (first row), and then stripped and re-blotted with anti-Fyn (second row); YT cell extracts were immunoprecipitated (IP) with anti-Lck antibodies and Western blotted with anti-phosphotyrosine antibodies (αPY) (third row), then stripped and re-blotted with anti-Lck antibodies (forth row). YT cells were cultured with vehicle only (lane a and b) or with ascending 649641P (NC1153) concentrations (1-100 μM) (lane c-i). These results show that 649641P (NC1153) does not block the activity of Fyn or Lck kinases.

The foregoing results show that while other inhibitors inhibited Jak3 and Jak2 responsive cell growth (IC$_{50}$ about 10-25 μM), 649641P (NC1153) was more effective by disrupting cell growth with an IC$_{50}$ about 2.5 μM. Moreover, 649641P (NC1153) effectively inhibited IL4 or IL7 driven cell growth at the same concentration (IC$_{50}$ about 2.5 μM). This agent inhibited tyrosine phosphorylation of Jak3 and its substrates, namely Stat5a/b, adapter protein Shc and Erk1/2, as measured by phospho-Western blots. 649641P (NC1153) was more effective that the previously described PNU156804 Jak3 inhibitor, displaying an IC$_{50}$ about 10 μM. Moreover, although Stat5a/b DNA binding to an oligonucleotide probe was greatly impaired by 649641P (NC1153), this compound was specific for this transcription factor since there was no effect on TNF-α-induced NF-kB DNA binding. The 649641P (NC1153) compound did not inhibit DNA synthesis of non-Jak3 expressing human Jurkat T-cells nor activation of TCR signaling intermediates Lck or Fyn tyrosine kinases.

EXAMPLE 2

Effect of Mannich Base 649461P (NC1153) on Allograft Survival

To test the in vivo effects, recipients of kidney allografts were treated with 649641P (NC1153) for 7 days beginning immediately after transplantation. ACI (RT1$^a$) recipients of LEW (RT1$^1$) kidney allografts were treated by daily i.v. injections for 7 days with 2.5, 5.0, 10.0, or 20.0 mg/kg 649641P (NC1153) alone or in combination with oral gavage of 2.5, 5.0, 10.0 or 20.0 mg/kg CsA. The 649641P (NC1153) given alone delivered by i.v. or oral gavage prolonged rat kidney allograft survival in a dose-dependent fashion, as shown in Table 1. Since 80 mg/kg 649641P (NC1153) p.o. produced similar survivals as 10 mg/kg 649641P (NC1153) injected i.v., the oral bioavailability is estimated to be approximately 12.5%. A mean survival time (MST) and SD was calculated for each group from 5-6 experiments. The combination index (CI) values were calculated by the median effect analysis (CI<1 shows synergistic, CI>1 antagonistic, and CI=1 additive interaction)[29,30].

TABLE 1

Kidney Allograft Survival
(Intravenous Administration of 649641P (NC1153))

| 649641P (NC1153) (mg/kg/d) i.v. × 7 days | CsA (mg/kg/d) p.o. × 3 days | 649641P:CsA Ratio | MST ± SD | P | CI |
|---|---|---|---|---|---|
| — | — | — | 8.8 ± 0.5 | — | — |
| 2.5 | — | — | 9.5 ± 1.5 | NS | — |
| 5.0 | — | — | 12.2 ± 1.5 | 0.01 | — |
| 10.0 | — | — | 18.8 ± 1.1 | 0.01 | — |
| 20.0 | — | — | 24.8 ± 4.6 | 0.01 | — |
| — | 2.5 | — | 12.6 ± 1.67 | 0.01 | — |
| — | 5.0 | — | 17.2 ± 4.21 | 0.01 | — |
| — | 10.0 | — | 21.7 ± 5.32 | 0.01 | — |
| — | 20.0 | 1:1 | 24.5 ± 4.58 | 0.01 | — |
| 2.5 | 2.5 | — | 18.8 ± 4.1 | 0.01 | 0.56 |
| 2.5 | 5.0 | 1:2 | 30.0 ± 8.2 | 0.01 | 0.21 |
| 2.5 | 7.5 | 1:3 | 30.4 ± 11.3 | 0.01 | 0.27 |
| 2.5 | 10.0 | 1:4 | 41.4 ± 9.8 | 0.01 | 0.11 |
| 5.0 | 2.5 | 2:1 | 20.0 ± 2.9 | 0.01 | 0.53 |
| 5.0 | 5.0 | 1:1 | 27.6 ± 5.3 | 0.01 | 0.38 |
| 5.0 | 7.5 | 1:1.5 | 33.2 ± 11.8 | 0.01 | 0.26 |
| 10.0 | 2.5 | 4:1 | 25.4 ± 4.0 | 0.01 | 0.60 |
| 10.0 | 5.0 | 2:1 | 29.8 ± 6.5 | 0.01 | 0.46 |

The effect on kidney allograft survival of 649641P (NC1153) alone, administered by oral gavage, or in combination with CsA is shown in Table 2. ACI (RT1$^a$) recipients of LEW (RT1$^1$) kidney allografts were treated once daily by oral gavage for 7 days with 40, 80, or 160 mg/kg/d. 649641P (NC1153) alone or in combination with oral gavage of 2.5, 5.0, 10.0 or 20.0 mg/kg/d CsA. A MST and SD were calculated for each group from 5-6 experiments. The combination index (CI) values were calculated.

TABLE 2

Kidney Allograft Survival
(Oral Gavage Administration of 649641P (NC1153))

| 649641P (NC1153) (mg/kg/d) p.o. × 7 days | CsA (mg/kg/d) p.o. × 3 days | 649641P:CsA Ratio | MST ± SD | P | CI |
|---|---|---|---|---|---|
| — | — | — | 8.8 ± 0.5 | — | — |
| 40.0 | — | — | 12.3 ± 1.26 | 0.0006 | — |
| 80.0 | — | — | 18.6 ± 5.32 | 0.0015 | — |
| 160.0 | — | — | 31.0 ± 3.9 | 0.0001 | — |
| — | 2.5 | — | 12.6 ± 1.67 | 0.0008 | — |
| — | 5.0 | — | 17.2 ± 4.21 | 0.0009 | — |
| — | 10.0 | — | 21.2 ± 4.96 | 0.0001 | — |
| — | 20.0 | — | 24.5 ± 4.28 | 0.0001 | — |
| 20.0 | 10.0 | 2:1 | 33.6 ± 10.04 | 0.0002 | 0.30 |
| 40.0 | 5.0 | 8:1 | 28.8 ± 9.87 | 0.0006 | 0.49 |
| 40.0 | 10.0 | 4:1 | 36.0 ± 10.05 | 0.0001 | 0.36 |
| 80.0 | 5.0 | 16:1 | 36.6 ± 4.72 | 0.0001 | 0.51 |

The results shown in Table 2 of MST±SD were assessed for statistical significance by Gehan's survival test.

Figure 5:
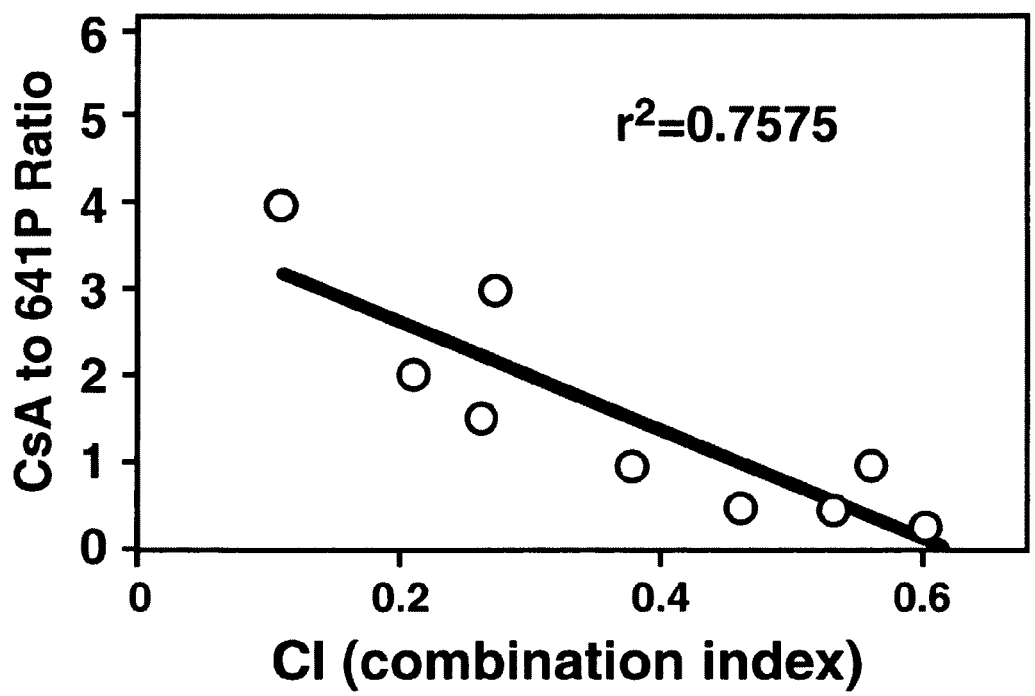
FIG. 5 is a graph showing the combination index for a range of CsA to 649641P (NC1153) ratios for survival of Lewis to ACI recipient rat heart allografts.

Combination index (CI) values versus CsA/649641P (NC1153) ratios calculated for the results presented in Table 1, and these data were graphed as shown in FIG. 5. Considering that CsA oral bioavailability is 90%, CsA/649641P (NC1153) ratio of 4:1, 3:1, 2:1 and 1.5:1 showed better synergism (CI=0.1-0.27) in comparison to CsA/649641P (NC1153) ratio of 1:1, 1:2, or 1:4 (CI=0.38-0.60). The median effect analysis and the combination index (CI) value were used to calculate the quality of interaction between 649641P (NC1153) and CsA. The combination of 649641P (NC1153) and CsA was synergistic, as confirmed by the CI values (0.6-0.1; FIG. 5); 649641P (NC1153)/CsA ratios of 1:2 to 1:4 were the most effective (CI=0.1-0.27; Table 1).

Summarizing the results, 649641P (NC1153) showed dose-dependent prolongation of kidney allograft survival: doses of 20 mg/kg/day 649641P (NC1153) delivered i.v. for 7 days produced a MST of 24.8±6.6 days (p=0.00003 vs. untreated control; MST=8.8±0.5 days) and 240 mg/kg/day 649641P (NC1153) delivered p.o. for 7 or 14 days, 47.8±19.59 or >60 days (both p<0.00001). Treatment with CsA alone (2.5, 5, 10, or 20 mg/kg/d for 3 days) produced dose-dependent effects achieving at the highest dose a MST of 24.50±4.58 days (p<0.0001). The combined treatments revealed a potent synergistic interaction in graft survival in comparison with monotherapy with each agent. For example, although a 7-day i.v. administration of 2.5 mg/kg/day 649641P (NC1153) alone produced a MST of 9.5±1.4 days, and a 3-day 10 mg/kg/day CsA alone of 21.2±5.3 days, two-drug combination prolonged survival to 41.4±9.8 days (p=0.00002). The best results were observed at 649641P:CsA dose ratios of 4:1 and 2:1, yielding the CI values of 0.11 and 0.27, respectively. It can be concluded that a new and selective Jak3 inhibitor, 649641P (NC1153), has been identified that is immunosuppressive in vivo in a kidney allotransplant model, and exerts marked synergistic effects in combination with CsA.

EXAMPLE 3

Evaluation of 649641P (NC1153) for Nephrotoxicity

Figure 6A:
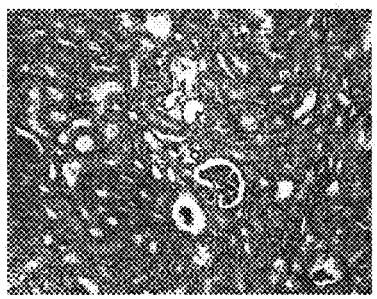
FIGS. 6A-E are photomicrographs (200× magnification) showing the effects of 649461P (NC1153), RAPA and CsA on rat kidney structure.
Figure 6B:
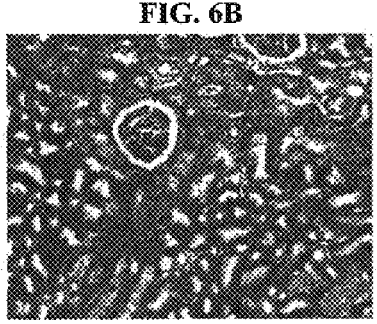
Figure 6C:
Figure 6D:
Figure 6E:
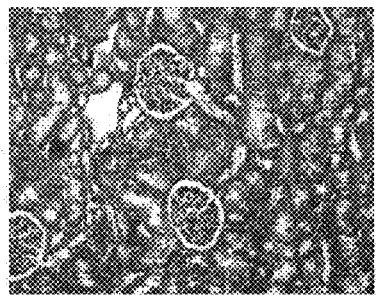

For histologic examination, tissue was obtained from ACI (RT1$^a$) recipients of LEW (RT1$^1$) kidney allografts that had been treated as follows: recipients on low-salt diet for 7 days were treated for 14 days with: 10 mg/kg 649641P (NC1153) delivered i.v.; 0.16 mg/kg RAPA delivered i.v.; 10 mg/kg CsA delivered p.o.; combination of 10 mg/kg CsA p.o. with 0.16 mg/kg RAPA i.v.; or combination of 10 mg/kg CsA p.o. with 10 mg/kg 649641P (NC1153) i.v. On day 14 rats were sacrificed and histology performed on kidneys using H&E staining in accordance with standard methods. The photomicrographs in FIGS. 6A-E show the effect of 649641P (NC1153) alone or in combination with CsA on kidney structure. All photographs are presented at the same 200× magnification. Similar results were observed in 5 rats per group. Neither 649641P (NC1153) (FIG. 6A) nor RAPA alone (FIG. 6B) showed any significant changes in the kidneys. In contrast, CsA alone (FIG. 6C) caused damage in 30% of tubuli as visualized by vacuolization and atrophy. The CsA/RAPA (SRL) group showed massive vacuolization in 90% of tubuli with atrophy and pyknotic nuclei (FIG. 6D). In contradistinction to the CsA/RAPA group, kidneys from rats treated with the CsA/649641P (NC1153) combination showed changes similar to those observed in the CsA alone group (FIG. 6E). In brief, neither 649641 or RAPA alone caused nephrotoxicity. CsA alone, however, was nephrotoxic, and this effect could be potentiated with RAPA but not with 649641P (NC1153).

In addition to the histologic studies described above, 649641P (NC1153)-treated animals were also evaluated for the types of toxicities that are typically associated with SRL. In this study, animal treatment included 649641P (NC1153) alone or in combination with CsA. Wistar-Furth rats received 649641P (NC1153) (10 mg/kg/d iv or 40/mg/kg/d per gavage) or SRL (1.6 mg/kg/d per gavage) alone or in combination with CsA (10 mg/kg/d per gavage). After 7 days of dietary preconditioning either by salt depletion (0.05% NaCl) to assess chronic nephrotoxicity or by fat supplementation (17.7% triglycerides, 5.02% cholesterol), groups of rats underwent 7, 14, or 28 day treatment courses (n=6/drug/duration). Differences in creatinine clearance (CrCL); total, low, and high density (HDL) cholesterol (CHOL) fractions; triglycerides (TG); bone marrow cellularity; peripheral blood counts (PBC); and blood chemistries were assessed by Fishers t test. The results of this study showed that 649641P (NC1153) caused weight gain (p=0.0002) and did not enhance the weight loss produced by CsA or SRL. CrCL values were similar for untreated (2.0 0.1 mL/min) and 649641P (NC1153) alone (1.9 0.1 mL/min), but decreased for SRL alone (1.7 0.1 mL/min; p<0.02), and CsA alone (1.3 0.1 mL/min; p<0.001). Compared with CsA alone, addition of 648641P did not further reduce CrCL values (1.38 0.2 mL/min; p=0.68); whereas, SRL markedly reduced it (0.9 0.2 mL/min; p=0.03). Compared to untreated rats on a low-salt diet, 649641P (NC1153) decreased serum CHOL (82.0 5.0 vs 65.5 9.4 mg/dL; p=0.03) and increased HDL (p=0.004) without changing TG or LDL levels. 648641P did not increase the hypercholesterolemic effects of CsA (77.5 7.0 alone vs 64.1 12.7 mg/dL in combination), in contrast to SRL+CsA (107.8 8.4 mg/dL; p=0.0005). On a high-fat diet, SRL produced a marked effect on CHOL (689.5 67.4; p=0.00001) and other lipid fractions; CsA, a lesser effect (545.7 95.7 mg/dL; p=0.0002) and 649641P (NC1153), only a modest change (323.8 51.1 mg/dL; p=0.01 vs 237.5 31.4 mg/dL) in untreated animals. 649641P (NC1153) had no effect on HDL, LDL, or TG levels. Neither 648641P nor CsA reduced PBC compared to untreated rats, in contrast to SRL (p<0.04). While SRL/CsA hosts showed hypocellular marrow (30-40% replaced by adipose tissue), 649641P/CsA cohorts showed no significant change from untreated rats. In view of these results, it was concluded that 649641P (NC1153) is free of nephrotoxic and myelotoxic effects with mild lipotoxicity on high-fat challenge. Since it does not exacerbate the adverse effects of CsA in the fashion that beclouds SRL, 649641P (NC1153) seems to exert selective actions on lymphoid elements.

From the foregoing investigations it can be concluded that 649641P (NC1153) blocks Jak3 activity, prolongs allograft survival alone and is synergistic with CsA. A preferred compound, 649641P (NC1153), showed in vitro selective inhibition of Jak3- compared to Jak2-dependent T-cell proliferation and in vivo extended survivals of organ allografts without causing any nephrotoxic side effects. Advantageously, 649641P (NC1153) displayed potent synergistic interaction with cyclosporine to prolong the survival of the organ allograft without increasing cyclosporine-induced nephrotoxicity. Moreover, 649641P (NC1153) shows greater specificity for blocking Jak3 but not Jak2 mediated cell activities than the previously described compounds AG490 and PNU156804. Although it is not clear at the present time whether the above-described desirable pharmacologic properties associated with the administration of 649641P (NC1153) are due entirely to the direct interaction of the 649641P (NC1153) compound with Jak3, or, for example, if Jak3 inhibition is mediated to any extent in vivo by a metabolite or derivative form of 649641P (NC1153). In the latter event, it is envisioned that direct administration of any such active metabolite or derivative species may be substituted therapeutically for 649641P (NC1153) if medically indicated. Likewise, a precursor compound that is acted on in vivo to yield one of the selective Jak3 inhibitor compounds described herein may also be administered therapeutically, if the particular needs of the individual so indicate.

EXAMPLE 4

Therapeutic Applications

The 649641P (NC1153) compound is considered representative of the medical usefulness of the group of compounds described herein for immunosuppressive therapies and for treating other pathologies of lymphoid, myeloid, or other cells containing or expressing Jak3. The compounds are considered especially useful in T-cell related diseases in humans, and for use in veterinary practice, for any application where it is desirable to suppress a Jak3-dependent lymphoid or myeloid cell function without affecting the activity of other protein kinases, or affecting such kinases to less, or therapeutically acceptable, extent. Treatment includes administering an amount of the compound effective to interfere with the signal 3 pathway in a lymphocyte, or other cell of lymphoid or myeloid origin which expresses Jak3, and thereby inhibit its function. For example, blocking cell division. Such administration may utilize the acid form of the compound or a pharmaceutically acceptable salt thereof, or it may be in the form of a biologically active metabolite of the compound. Alternatively, a precursor compound may be administered which is capable of being metabolized in the body of the subject to one or more active forms of the compound, whereby a Jak3-dependent lymphocyte function is disrupted, preferably blocking cell division. Administration may be continuous or periodic.

In some medical situations, the individual will be in need of suppression of an undesirable immune response, in which case administration of an effective amount of a pharmaceutical composition containing 649641P (NC1153), or a precursor or active metabolite will mitigate or prevent the unwanted immune response. By co-administering a therapeutically effective amount of a different immunosuppressive agent, such as cyclosporin A or FK506, which do not act via Jak3 inhibition, even better results may be achieved with less toxicity to the individual. Examples of such use include mitigating organ transplant rejection or allograft rejection in a mammalian transplant or allograft recipient, or to induce transplantation tolerance. In other instances, the therapeutic goal may be to promote remission of an autoimmune disease mediated by endogenous Jak3-dependent T-cells so that the autoimmune attack on the subject's native tissue is diminished or arrested. Still other avenues of use include administering a pharmaceutical preparation of 649641P (NC1153) to mitigate airway hypersensitivity in a mammalian subject by suppressing a T-cell mediated hypersensitivity response. Similarly, allergy sufferers may be treated to suppress a T-cell mediated allergic response and thereby diminish or arrest the allergic reaction. Administration of a pharmaceutical composition containing 649641P (NC1153) is also expected to inhibit proliferation of Jak3-dependent leukemia or lymphoma. A notable potential advantage of therapeutic treatment with 649641P (NC1153) is that by selectively inhibiting Jak3 activity, which is limited to cells of the lymphoid compartment (and Jak3 expressing myeloid cells), and having little or no effect on Jak2, and other protein kinase activities found in many tissues throughout the body, far fewer side effects are expected.

Pharmaceutical compositions. A pharmaceutical composition suitable for therapeutic use contains the 649641P (NC1153) compound in its acid form, or a pharmaceutically acceptable salt or hydrate thereof, in combination with a suitable carrier. Pharmaceutically acceptable salts and hydrates refer to those salts and hydrated forms of the compound which would be apparent to the pharmaceutical chemist, i.e., those which favorably affect the physical or pharmacokinetic properties of the compound, such as solubility, palatability, absorption, distribution, metabolism and excretion. Other factors, more practical in nature, which are also important in the selection of the form of the compound include the cost of the raw materials, ease of crystallization, yield, stability, solubility, hygroscopicity and flowability of the resulting bulk drug. When the compound is negatively charged, it is balanced by a counterion, e.g., an alkali metal cation such as sodium or potassium. Other suitable counterions include calcium, magnesium, zinc, ammonium, or alkylammonium cations such as tetramethylammonium, tetrabutylammonium, choline, triethylhydroammonium, meglumine, triethanolhydroammonium, etc. An appropriate number of counterions is associated with the molecule to maintain overall charge neutrality. Likewise when the compound is positively charged, e.g., protonated, an appropriate number of negatively charged counterions is present to maintain overall charge neutrality.

Pharmaceutically acceptable salts also include acid addition salts. Thus, the compound can be used in the form of salts derived from inorganic or organic acids or bases. Examples include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

A Jak3 inhibitor compound described herein may be formulated in a pharmaceutical composition by combining the compound with a pharmaceutically acceptable carrier, as are known in the art. The compounds may be employed in powder or crystalline form, in solution or in suspension. They may be administered orally, parenterally (intravenously or intramuscularly), topically, transdermally or by inhalation. The carrier employed may be, as appropriate, a solid or liquid. Examples of solid carriers include lactose, terra alba, sucrose, talc, gelatin, agar, pectin, acacia, magnesium stearate, stearic acid and the like. Examples of liquid carriers include syrup, peanut oil, olive oil, water and the like. A carrier for oral use may include time delay material well known in the art, such as glyceryl monostearate or glyceryl distearate alone or with a wax. Topical applications may be formulated in carriers such as hydrophobic or hydrophilic bases to form ointments, creams, lotions, in aqueous, oleaginous or alcoholic liquids to form paints or in dry diluents to form powders. Examples of oral solid dosage forms include tablets, capsules, troches, lozenges and the like. The size of the dosage form will vary widely, but preferably will be from about 25 mg to about 500 mg. Examples of oral liquid dosage forms include solutions, suspensions, syrups, emulsions, soft gelatin capsules and the like. Examples of injectable dosage forms include sterile injectable liquids, e.g., solutions, emulsions and suspensions. Examples of injectable solids include powders which are reconstituted, dissolved or suspended in a liquid prior to injection. In injectable compositions, the carrier is typically comprised of sterile water, saline or another injectable liquid, e.g., peanut oil for intramuscular injections. Also, various pharmaceutically acceptable buffering agents, preservatives and the like may be included.

Dosage. Pharmaceutical compositions for implementing the therapeutic use of the Jak3-selective inhibitor compounds described herein include compositions contain the active ingredients in an amount sufficient to achieve the intended purpose, i.e., the selective disruption or inhibition of Jak3 activity or the treatment or prevention of a Jak3-related disorder. A therapeutically effective amount or dose can be estimated initially from cell proliferation assays, as presented herein. Then, the dosage can be formulated for use in animal models so as to achieve a circulating concentration range that includes the $IC_{50}$ as determined in cell culture (i.e., the concentration of the compound which achieves a half-maximal inhibition of IL2 dependent proliferation and little or no inhibition of PRL dependent proliferation), as also demonstrated herein. Such information may then be used to more accurately determine a range of useful doses in humans and other mammals, in accordance with standard pharmacologic practices. The dosage may vary depending upon the dosage form employed and the route of administration utilized. For instance, dosage amount and intervals may be adjusted individually to provide plasma levels of the active species which are sufficient to initiate and/or maintain the desired Jak3 inhibitory effects. These plasma levels are customarily referred to as minimal effective concentrations (MECs). The MEC may vary from one compound to another, but may be estimated from in vitro data, as noted above. For example, the concentration necessary to achieve 50-90% inhibition of Jak3 autokinase activity in a population of T-cells may be ascertained using the assays described herein. HPLC assays or bioassays may be employed to determine plasma concentrations. Dosage intervals can also be determined using MEC value. Preferably the compound will be administered using a regimen that maintains plasma levels above the MEC for the desired period of time. In treatments which include local administration or selective uptake, the effective local concentration of the compound, or its active metabolite or derivative, may not be adequately reflected by plasma concentration. In this case, other procedures which are known in the art may be employed to determine an appropriate dosage amount and interval. An example of a suitable oral dosage range for an adult human is from about 0.1 to about 80 mg/kg per day, in single or divided doses. An example of a suitable parenteral dosage range is from about 0.1 to about 80 mg/kg per day, in single or divided dosages, administered by intravenous or intramuscular injection. An example of a topical dosage range is from about 0.1 mg to about 150 mg, applied externally from about one to four times a day. An example of an inhalation dosage range is from about 0.01 mg/kg to about 1 mg/kg per day. The exact formulation, route of administration and dosage can be chosen by the individual physician in view of the patient's condition, the nature of the illness being treated, and other factors.

EXAMPLE 5

Additional Jak-3 Selective Inhibitor Compounds

In the preceding Examples it was demonstrated that 649641P (NC1153) selectively or specifically inhibits the proliferation and function of Jak3-containing T-cells, prolongs allograft survival, and demonstrates low toxicity. In view of these evaluations, it is clear that 649641P (NC1153) has probable therapeutic value for treating individuals having immune-related disorders. This compound is also valuable as a reagent for use as a standard for comparison in evaluating other candidate drug compounds with respect to selectivity for inhibition or disruption of Jak3 in vitro assays and in vivo studies.

As noted above, in the course of the present investigations the NCI Drug Discovery Database was scanned for additional candidate compounds that might serve as selective inhibitors of Janus kinase 3 (Jak3). Compounds that displayed a similar correlation coefficient to the "seed" compound AG490, a tyrphostin with Jak3 inhibitory potential, were assessed.

COMPARE Algorithm. The NCI drug database is comprised of hundreds of thousands of compounds that have been gathered from various sectors of the world. These include donations of drugs that range from large pharmaceutical companies to small privately owned laboratories. In many instances these compounds were added to test and promote the library. However, many of these compounds have been discontinued by the manufacturer due to ineffectiveness for its originally proposed function and in some instances the submitting company is no longer in operation. Regardless of the status of the drug, its structure and resulting activity has been added to the library database which is updated weekly.

The database was generated by testing a dose response for a particular drug against 60 distinct human cell lines (e.g., epithelial, lung, colon, monocyte/macrophage, T-B cells, breast-prostrate, etc). Three parameters are measured include inhibition of cell growth ($IC_{50}$), cytotoxic ($LC_{50}$), and cytostatic effects (TGI). Together, they comprise a mean graph "signature" for each compound. Drugs that display a positive value (project to the right) are reflective cellular sensitivities that exceed the mean. Negative values (project to the left) indicate that cell lines are less sensitive to the test agent than the average. COMPARE is an algorithm that rank-orders each compound based on its activity in vitro to a predetermined "seed", as in the present case AG-490. Mean graphs are converted for each drug to a scalar index rating using. Pearson's correlation coefficient (PCC). Ultimately, drugs with the most similar effects will show high-ranking correlation (approaching 1) and likely to possess mechanisms of action similar to that of the seed compound.

COMPARE has been successful in identifying compounds with similar mechanisms of action. This is a hypothetical model based on the premise that similar drugs that, for example, block cell growth will target the same critical target pathway in a similar cell type. Cells that rely heavily on a particular pathway will be sensitive to inhibition of that pathway (such as cells that express JAK3/Stat5), whereas cells that fail to express such molecules or are less dependent on this pathway, the same drugs will have little or no effect. This allows COMPARE to group together drugs with similar mechanisms of action across a panel of cells.

A number of different studies completed to date have shown that this approach has been successful for identifying new agents which selectively affect the same molecular target, thus yielding a distinctive mean graph pattern. The COMPARE algorithm can identify similar mean patterns for a compound of distinct structure, but with the same mechanism of action compared to the seed. Laboratory studies need to confirm the match within a particular read-out (JAK3 Stat5 phosphorylation). COMPARE does not necessarily rely on chemical structure as it does similar mechanisms of drug action. This allows for identification of structurally novel classes of compounds that were never before recognized as a particular inhibitor for a given target. The effectiveness of this approach has been borne out by identifying inhibitors of p53, Raf, topoisomerase, and tubulin binding proteins. Once a structural class of known mechanisms of action is discovered then additional screening of available analogues and synthesis of new ones can be used to define and optimize a drug of interest.

Among the compounds identified in the above-mentioned NCI drug database screening were 649641P (NC1153) and several congeners or structural analogs of 649641P. The effect of the compounds 637712, 640674, 643423, 655906, 673137, 683332 and 693812 (denoted by their NCI database numbers) on T-cell proliferation was assessed and compared to the effects of AG490, PNU156804 and 649641P (NC1153). The results of those comparative assays are shown in bar graph form in FIG. 7A. It can be seen that proliferation of PHA-activated human T cells is blocked by these NCI agents following stimulation with IL-2. The structural formula of NC1153 is shown in the inset. NC1153 failed to affect IL2 receptor expression.

Figure 7A:
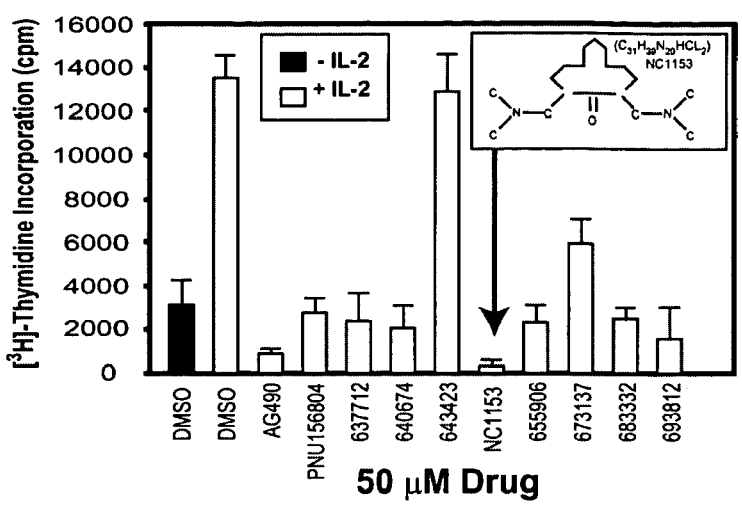
FIGS. 7A-D are graphs showing that 649641P (NC1153) specifically inhibits growth of Jak3 containing T-cells.
Figure 7B:
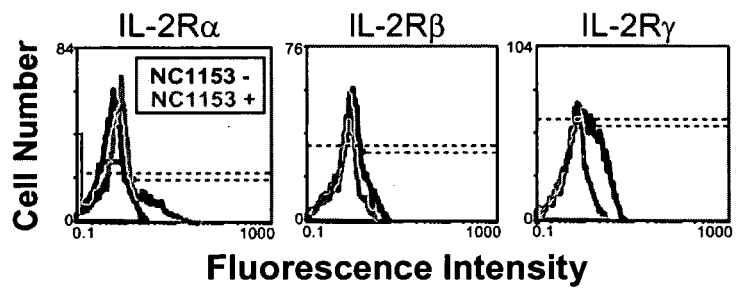
Figure 7C:
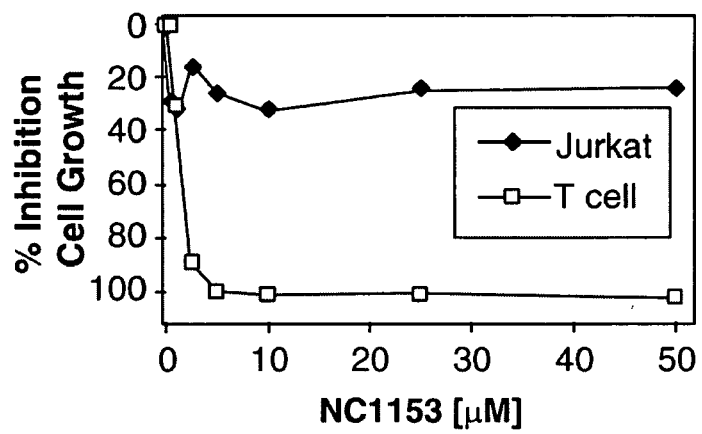
Figure 7D:
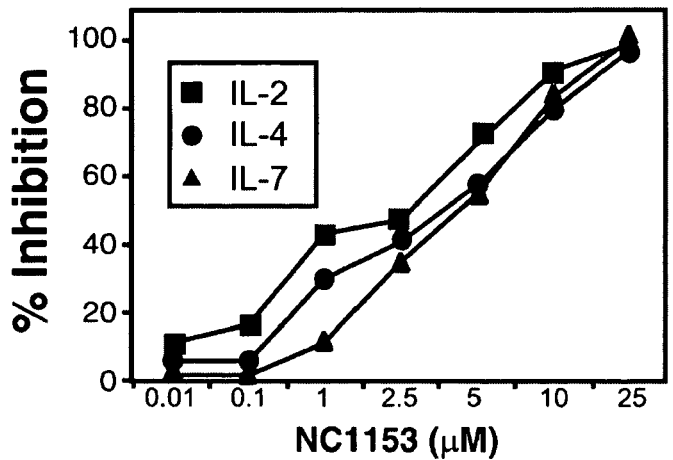

Also shown (FIG. 7B) is a graph showing the FACS analysis of PHA-activated T-cell blasts that were treated without (heavy line) or with 50 μM NC1153 (light line) overnight and stained for IL2R-α, -β, and -γ chains. The dashed lines indicate cells pretreated with NC1153. These results show that the presence of the IL-2 receptors is unaffected by the NC1153. These findings demonstrate that the loss of IL2 signals is not due to changes in receptor expression, thus occurring distal to the IL2 receptor, hence Jak3. As shown in FIG. 7C, the NC1153 compound does not block cell growth of non-Jak3 expressing cells. Jurkat cells (black diamonds) which fail to express Jak3 do not show significant change in cell growth following treatment with NC1153 in contrast to Jak3 containing PHA activated T-cells (open boxes). Data are normalized as percent of vehicle control. NC1153 inhibits growth of cells by cytokines that utilize Jak3 and the common gamma chain (FIG. 7D). As also shown in FIG. 1A, T-cell proliferation of 649641P (NC1153) treated T-cells inhibits IL2, IL4 or IL7 driven growth normalized to untreated controls in a dose dependent manner. Thus, the inhibitory effects of NC1153 are not limited to cells stimulated only by IL-2. Instead, the entire family of cytokines which use Jak3 are blocked by NC1153.

Figure 8:
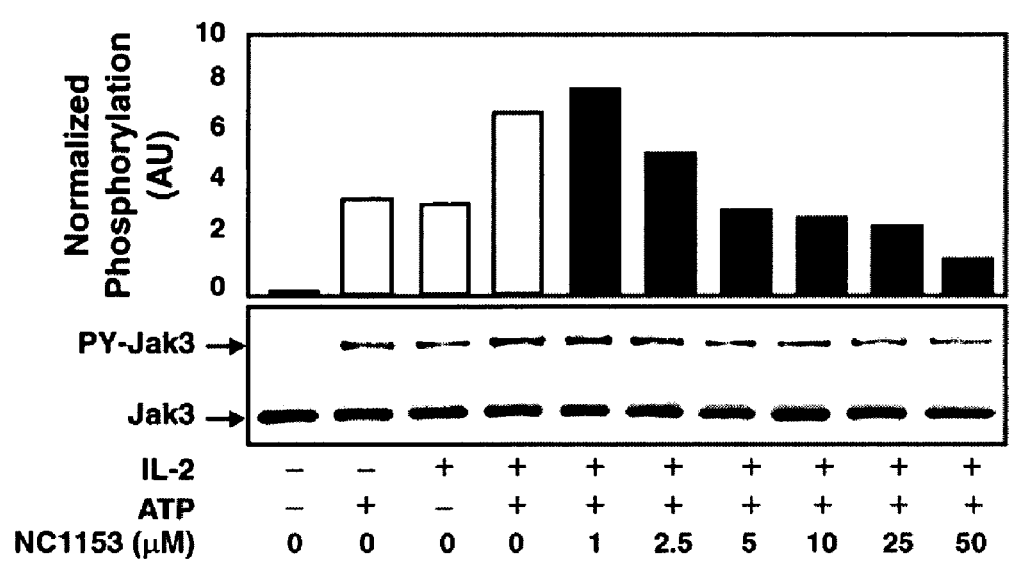
FIG. 8 is a bar graph showing that Jak3 autokinase activity is directly blocked by 649641P (NC1153) based on in vitro analysis. Immunopurified Jak3 was assayed for Jak3 autokinase activity and tested by phosphotyrosine Western blot in the absence or presence of 100 µM ATP and/or drug and compared to controls. 649641P (NC1153) showed an $IC_{50}$ of approximately 2.5 µM, which parallels the proliferation data of FIGS. 1A and B.

Referring now to FIG. 8, direct evidence is provided that 6496421P (NC1153) inhibits Jak3 signaling pathways. Jak3 autokinase activity is directly blocked by NC1153 based on in vitro analysis. The bands identified as "PY-Jak3" reveal only the active Jak3 at the indicated dosages of NC1153, with or without IL-2 and ATP. The bands identified as "Jak3" reveal the presence of total (active plus inactive) Jak3 protein. To show that inhibiting Jak3 blocks downstream pathways, immunopurified Jak3 was assayed for Jak3 autokinase activity and tested by phosphotyrosine Western blot in the absence or presence of 100 μM ATP and/or drug and compared to controls, as shown in FIGS. 2A-C. It was also observed that 649641 (NC1153) showed an $IC_{50}$ of approximately 2.5 μM that parallels the proliferation data, as shown in FIGS. 7A and 7D.

Figure 9A:
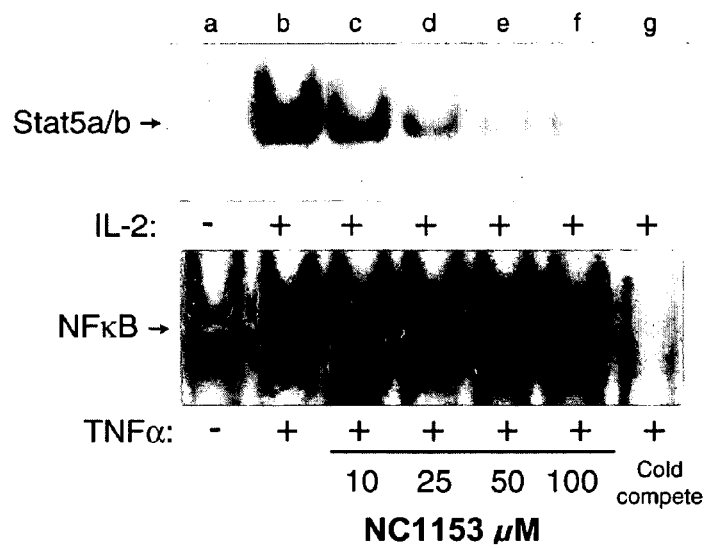
FIGS. 9A-C demonstrate 649641P (NC1153) selectivity.
Figure 9B:
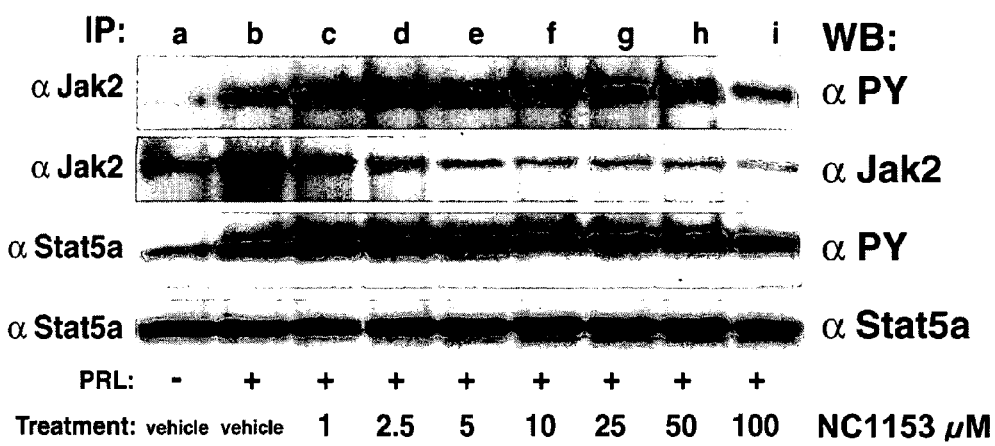
Figure 9C:
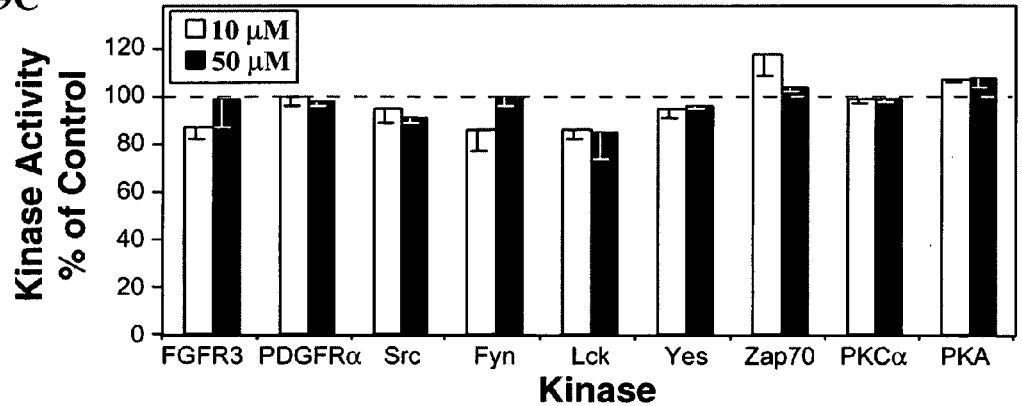

FIGS. 9A-C show that NC1153 does not inhibit non-Jak3 signaling pathways. In FIG. 9A, it can be seen that NC1153 inhibits Jak3 driven transcription factor-Stat5a/b in PHA activated T-cells treated with increasing concentrations of NC1153 in a dose dependent manner as measured via EMSA analysis (upper panel). The lane identified as "cold compete" contains unlabeled probe. However, non-Jak3 mediated NfκB activation (lower panel) by TNF-α was not affected within the same treatment set. The results shown in FIG. 9B establish that NC1153 fails to inhibit the closely related Jak2/Stat5a signaling pathway. Rat Nb2 cells were treated with increasing concentration of NC1153 and then stimulated with prolactin. Phosphotyrosine Western blots detect activation but no inhibition by NC1153. In Stat5a/b activation Jak3 mediated Jak3 autokinase activity is directly blocked by NC1153 based on in vitro analysis. NC1153 fails to affect activity of multiple kinases. At least 50 fold more inhibition of Jak3 than Jak2 in kinase assays is shown in FIG. 9B and FIG. 8. As shown in FIG. 9C, NC1153 was tested at 10 or 50 μM to block growth factor tyrosine kinases (FGFR3 and PDGFRα), Src family tyrosine kinases (Src, Fyn, Lck, Yes, Zap70) or serine threonine kinases (PKC and PKA) phosphorylation of a substrate. Activity of the control is plotted as a dashed line.

Figure 10A:
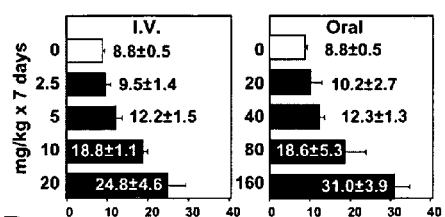
FIGS. 10A-D illustrate the in vivo effects of NC1153 on allograft survival.
Figure 10B:
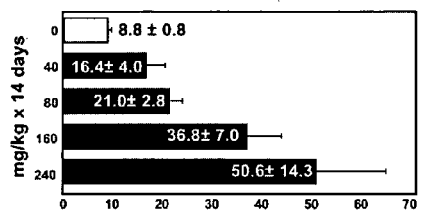
Figure 10C:
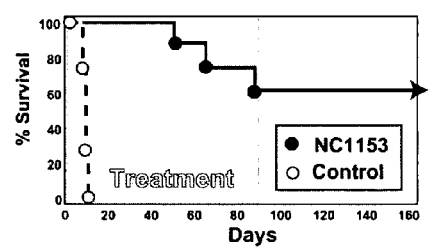
Figure 10D:
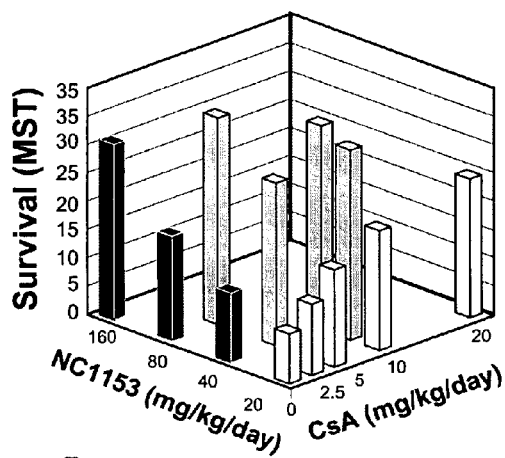

FIGS. 10A-D summarize the in vivo effects of 649641P (NC1153) on allograft survival (presented in Table 1.) ACI rat recipients of Lewis (LEW) kidney allografts were treated for 7 days with NC1153 delivered by daily i.v. injections or by oral gavage. Allograft survival time (days) at varying drug dosage is shown in FIG. 10A, and individual survivals are shown in Table 1. ACI rat recipients of LEW kidney allografts were treated for 14 days with NC1153 delivered by daily oral gavage. The graft survival rate (days) is shown at varying dosages of NC1153) in FIG. 10B. ACI rat recipients of LEW kidney allografts were treated for 7 days and thereafter 3x/week up to 90 days with 160 mg/kg NC1153 delivered by daily oral gavage. As shown in FIG. 10C, 75% of the treated recipients survived to beyond treatment of 90 days with survival times exceeding 200 days. Induction of transplantation tolerance was confirmed by acceptance of LEW donor-(>100 days; n=3) but not third-party BUF (7.0±1.0 days; n=3) heart allografts by long-term surviving recipients. The mechanism of tolerance was examined when irradiated (400 rads) ACI recipients of $LEW_6$ heart allografts were adoptively transferred with $30 \times 10^6$ purified T cells from tolerant recipients. Recipients transferred with tolerant T cells displayed significantly delayed rejection of LEW heart allografts (40.0±15.0 days; n=6 vs 15±1.0 days; n=5 in irradiated controls) with 2 hearts beating well for >100 days, but rejected third-party heart allografts (12±1.0 days; n=2). These results suggest that transplantation tolerance was mediated at least in part by T cell regulatory cells (not shown). FIG. 10D shows a summary of the results presented above in Table 2 regarding ACI rat recipients of LEW kidney allografts treated for 7 days with NC1153 alone, with CsA alone, and with the combined drugs, delivered by daily oral gavage. The MST of each treatment group at each dosage level is shown and below chart display the low CI values indicating that the NC1153-CsA combination is synergistic.

As shown in FIGS. 11A-F, 649641P (NC1153) is not nephrotoxic and does not affect lipid metabolism. Rats fed low-salt diet (7 days prior and during 14 day therapy) were treated by oral gavage with 160 mg/kg NC1153 alone or in combination with 5 mg/kg CsA; some animals were treated by oral gavage with 0.8 mg/kg rapamycin (RAPA) alone or in combination with 5 mg/kg CsA. Kidney function was evaluated by serum creatinine levels and serum creatinine clearance, and the results are shown in FIGS. 11A and 11B, respectively. Lipid metabolism was evaluated by measuring of serum cholesterol (FIG. 11C), triglycerides (FIG. 11D), LDL-cholesterol (FIG. 11E), and HDL-cholesterol (FIG. 11F). The effect of NC1153 alone or in combination with CsA on kidney structure was determined. Rats on low-salt diet for 7 days were treated for 14 days with: 10 mg/kg NC1153 delivered i.v.; 0.16 mg/kg RAPA delivered i.v.; 10 mg/kg CsA delivered by oral gavage; combination of 10 mg/kg CsA p.o. with 0.16 mg/kg RAPA i.v.; or combination of 10 mg/kg CsA p.o. with 10 mg/kg 641P i.v. On day 14 rats were sacrificed and histology performed on kidneys using H&E staining. Similar results were observed in 5 rats per group. As shown in FIGS. 6A-E, neither 649641P (NC1153) alone nor RAPA alone showed any significant changes in the kidneys. In contrast, CsA alone caused damage in 30% of tubuli with vacuolization and atrophy. The CsA/RAPA group showed massive vacuolization in 90% of tubuli with atrophy and pyknotic nuclei. In contradistinction to the CsA/RAPA group, kidneys from rats treated with the CsA/NC1153 combination showed changes similar to those observed in the CsA alone group.

The meso stereoisomer of 649641P (NC1153), designated WP938 (shown in FIG. 18B) was synthesized using a procedure which included the following steps: to 0.1 mmol of cycloalkanoneone and 0.21M of N,N,N',N'-tetramethyl-diaminomethane dissolved in 400 mL of acetonitrile was added dropwise in 40 minutes 16.5 g (0.21 mol) of acetyl chloride. After reaction was completed the crude product precipitated, filtered, washed with ether and dried. Subsequent crystallizations led to pure product.

The resulting WP938 compound was tested for its effect on allograft survival and for toxicities, when administered alone or in combination with CsA. The results are shown in FIGS. 12A,B-13A-F. It was found that WP938 alone delivered by oral gavage for 7 days at doses 20-160 mg/kg extended in dose-dependent fashion the survivals of ACI recipients of LEW kidney allografts (FIG. 12A). Combination of 1.25 mg/kg CsA and 160 mg/kg WP938 delivered p.o. for 7 days produced synergistic interaction on kidney allograft survival, as documented by the CI value of 0.44. (FIG. 12B) As shown in FIGS. 13A-F, a 14-day oral therapy with 160 mg/kg WP938 produced no changes in chemistries and blood elements counts documenting lack of toxicities. Serum creatinine and creatinine clearance showed lack of nephrotoxcicity by WP938 and no effect on CsA-induced nephrotoxicity. (FIGS. 13A,B). FIG. 13C indicates cholesterol levels. FIG. 13D indicates triglyceride. FIG. 13E indicates HDL levels. FIG. 13F indicates LDL levels.

FIG. 14B through FIG. 39B show the chemical formulas of various Mannich base compounds and others (shown as salts) that were screened for ability to inhibit proliferation in prolactin or IL2 stimulated T-cells. FIGS. 14A through 39A show the results of those assays over the indicated concentration range. The screening assays were carried out substantially as described in the general methods, above. Compounds having the apparent characteristic of not blocking Jak2 and Stat5a/b activation by prolactin (PRL) (dark squares) at concentrations sufficient to inhibit Jak3 and Stat5a/b activated by IL2 (light squares) were identified for further evaluation. The preferred 649641P (NC1153) compound and its selective inhibitory activity are shown in Example 1 and FIGS. 1A,B. Additional candidate drugs, the compounds shown in FIGS. 14B-17B and 19B-39B, which demonstrated at least some amount of selective inhibitory activity with respect to PRL or IL2 stimulated T-cells at specified concentrations, are the subject of ongoing investigations in the same manner as described in the foregoing examples employing the representative compound 649641P (NC1153). Where applicable, these compounds may have asymmetric centers and occur as racemates, racemic mixtures and as individual diastereomers, or enantiomers with all isomeric forms being included, for the purposes disclosed herein. For example, with respect to Formula (I), the configuration at C-2 and C-12 may be (R) or (S). These compounds, including all stereoisomers, which are determined to be sufficiently non-toxic and which are able to significantly prolong allograft survival as demonstrated herein for 649641P (NC1153) will also have probable therapeutic value in humans and for veterinary use in immunosuppressive therapies. They are also expected to be of therapeutic value for treating other pathologies related to Jak3 expressing cells of lymphoid or myeloid origin. As was demonstrated for 649641P (NC1153) and WP938, it is believed that some of these candidate drug compounds will also demonstrate synergistic activity when administered with CsA or other immunosuppressive agents that exert their immunosuppressive effects by pathways other than Jak3-related pathways.

Definitions

In addition to having their customary and usual meaning, the following definitions apply where the context permits in the specification and claims:

"Selective inhibition" refers to a chemical compound that preferentially blocks the function of one protein and to a lesser degree one or more known proteins.

"Specific inhibition" refers to a chemical compound that solely blocks the function of a given protein without affecting other proteins.

"Immunosuppressive potential" refers to a chemical compound that should reduce or ablate an immune response (e.g. a drug that blocks rejection of a transplanted organ allograft).

"Pharmaceutical composition" refers to a mixture of one or more chemicals, or pharmaceutically acceptable salts thereof, with a suitable carrier, for administration to a mammal as a medicine.

"Lymphoid cells" refer to cells of immune origin, or, more specifically, cells derived from stem cells of the lymphoid lineage, including large and small lymphocytes and plasma cells. Examples of lymphoid cells are T-cells, B-cells and natural killer (NK) cells.

"Myeloid cells" refers to cells of myeloid origin, i.e., derived from stem cells of myeloid lineage, including monocytes, macrophages and dendritic cells.

"Drug" refers to a chemical compound suitable for medical use.

"Congener" or cogener refers to a chemical compound closely related to another in composition (e.g., a structural analog) and exerting similar or antagonistic effects.

"Therapeutically effective amount" refers to that amount of the compound being administered that will relieve at least to some extent one or more of the symptoms of the disorder being treated. For example, an amount of the compound effective to prevent, alleviate or ameliorate symptoms of disease or prolong the survival of the subject being treated.

With respect to a disease or disorder, the term "treatment" refers to preventing, deterring the occurrence of the disease or disorder, arresting, regressing, or providing relief from symptoms or side effects of the disease or disorder and/or prolonging the survival of the subject being treated.

REFERENCES

1. Kane L P, Lin J, Weiss A. Signal transduction by the TCR for antigen. Curr Opin Immunol. (2000) 12L2420249.
2. Denton, M D, Magee C C, Sayegh M H. Immunosuppressive strategies in transplantation. Lancet (1999) 353: 1083-1091.
3. Mihatsch M J, Kyo M, Morozumi K, et al. The side effects of Cyclosporin-A and Tacrolimus. (1998) Clin. Nephrol 49:356-363.
4. Kahan B D, Camardo J S. Rapamycin: clinical results and future opportunities. Transplantation (2001) 72:1181-1193.
5. Kirken R A, Stepkowski S M. New directions in T-cell signal transduction and transplantation tolerance. Transplant (2002) 7:18-25.
6. Weiss A, Littman D R. Signal transduction by lymphocyte antigen receptors. Cell. (1994) 76:263-274.
7. Irving B A, Chan A C, Weiss A. Functional characterization of a signal transducing motif present in the T cell antigen receptor zeta chain. J Exp Med. (1993) 177:1093-1103.

8. Chan A C, Kadlecek T A, Elder M E, et al. ZAP-70 deficiency in an autosomal recessive form of severe combined immunodeficiency. Science. (1994) 264:1599-1601.
9. Appleby M W, Gross J A, Cooke M P, Levin S D, Qian X, Perlmutter R M. Defective T cell receptor signaling in mice lacking the thymic isoform of p59fyn. Cell. (1992) 70:751-763.
10. Kuo C T, Leiden J M. Transcriptional regulation of T lymphocyte development and function. Annu Rev Immunol. (1999) 17:149-187.
11. Leonard W J, O'Shea J J. JAKs and STATs: biological implications. Annu Rev Immunol. (1998); 16:293-322.
12. Kondo M, Takeshita T, Ishii N, et al. Sharing of the interleukin-2 (IL-2) receptor gamma chain between receptors for IL-2 and IL-4. Science. (1993) 262:1874-1877.
13. Noguchi M, Nakamura Y, Russell S M, et al. Interleukin-2 receptor gamma chain: a functional component of the interleukin-7 receptor. Science. (1993); 262:1877-1880.
14. Russell S M, Keegan A D, Harada N, et al. Interleukin-2 receptor gamma chain: a functional component of the interleulin-4 receptor. Science. (1993) 262:1880-1883.
15. Russell S M, Johnston J A, Noguchi M, et al. Interaction of IL-2R beta and gamma c chains with Jak1 and Jak3: implications for XSCID and XCID. Science. (1994) 266: 1042-1045.
16. Kirken R A, Rui H, Malabarba M G, et al. Activation of JAK3, but not JAK1, is critical for IL-2-induced proliferation and STAT5 recruitment by a COOH-terminal region of the IL-2 receptor beta-chain. Cytokine. (1995) 7:689-700.
17. Malabarba M G, Rui H, Deutsch H H, et al. Interleukin-13 is a potent activator of JAK3 and STAT6 in cells expressing interleukin-2 receptor-gamma and interleukin-4 receptor-alpha. Biochem J. (1996) 319:865-872.
18. Szabo S J, Glimcher L H, Ho I C. Genes that regulate interleukin-4 expression in T cells. Curr Opin Immunol. (1997) 9:776-781.
19. Kirken R A, Rui H, Malabarba M G et al. J Biol Chem (1994) 269:19136.
20. Johnston J A, Kawamura M, Kirken R A, et al. Nature (1994) 370:151.
21. Kirken R A. Transplantation Proceedings (2001) 33:3268-3270.
22. Thomis T C, Berg L J. Curr Opin Immunol (1997) 9:541.
23. Kirken R A, Erwin R A, Taub D, et al. Tyrphostin AG490 inhibits cytokine-mediated Jak3/Stat5a/b signal transduction and cellular proliferation of antigen-activated human T-cells. J Leukoc Biol (1999) 65:891-899.
24. Behbod F, Erwin-Cohen R A, Wang M -E, et al. Concomitant inhibition of Janus kinase 3 and calcineurin-dependent signaling pathways synergistically prolongs the survival of rat heart allografts. J Immunol (2001) 166:3724-3732.
25. Stepkowski S M, Erwin-Cohen R A, Behbod F et al. Selective inhibitor of Janus tyrosine kinase 3, PNU156804, prolongs allograft survival and acts synergistically with cyclosporine but additively with rapamycin. Blood (2002) 99:680-689.
26. Yamashita H, Xu J, Erwin R A, Farrar W L, Kirken R A, Rui H. Differential control of the phosphorylation state of proline-juxtaposed serine residues Ser725 of Stat5a and Ser730 of Stat5b in prolactin-sensitive cells. J Biol. Chem. (1998) 273:30218-30224.
27. Kirken R A, Rui H, Malabarba M G, et al. Activation of JAK3, but not JAK1, is critical for IL-2-induced proliferation and STAT5 recruitment by a COOH-terminal region of the IL-2 receptor beta-chain. Cytokine. (1995) 7:689-700.
28. Ono K, Lindsey E S. Improved technique of heart transplantation in rats. J Thorac Cardiovasc Surg. (1969) 57:225-229.
29. Chou T -C. The median effect principle and the combination index for quantitation of synergism and antagonism. In: Chou T -C, Rideout D, Eds. Synergism and antagonism in chemotherapy. San Diego, Calif.: Academic Press, Inc, 1991:61-102.
30. Chou J, Chou T -C. Dose-effect analysis with microcomputers: quantitation of ED50, LD50, synergism, antagonism, low-dose risk, receptor-ligand binding and enzyme kinetics. Biosoft, Cambridge, UK. 1987.
31. Schrader B, Steinhoff G. Models of inflammatory cascade reactions by adhesion molecules. In: Steinhoff G, Ed. Cell adhesion molecules in human organ transplants. Austin: R G Lands Company, 1993:71-86.
32. Winters G L, Marboe C C, Billingham M E. The international society for heart and lung transplantation grading system for heart transplant biopsy specimens: Clarification and commentary. J Heart Lung Transplant. 1998; 17:754-760.
33. Thomis D C, Berg L J. Peripheral expression of Jak3 is required to maintain T lymphocyte function. J Exp Med (1997) 185: 197-206.
34. Dimmock J R, Kumar P. Anticancer and Cytotoxic Properties of Mannich Bases. Current Medicinal Chemistry (1997) 4:1-22.
35. Dimmock J R, Chamankhah M, Seniuk A et al. Synthesis and Cytotoxic Evaluation of Some Mannich Bases of Alicyclic Ketones. Pharmazie (1995) 50:668-671.

While the preferred embodiments of the invention have been shown and described, modifications thereof can be made by one skilled in the art without departing from the spirit and teachings of the invention. The embodiments described herein are exemplary and representative, and are not intended to be limiting. Many variations and modifications of the invention disclosed herein are possible and are within the scope of the invention. Although the foregoing discussion focuses on T-cell derived graft vs. host disease, it will be readily appreciated that the methods, compounds and compositions described herein are also likely to have application in other T-cell dependent diseases or disorders. For example, they may be useful for treating autoimmune diseases such as lupus, arthritis and multiple sclerosis, or for treating allergy, asthma, psoriasis, ulcerative colitis, lymphomas, and leukemias. Selective Jak3 targeted inhibition is also expected to also have application in many other immune-derived pathologies, or in Jak3 expressing myeloid cell derived pathologies, including hyperactive immune system responsive conditions derived from hyperactive or unwanted dendritic cell, B-cell, monocyte, macrophage or natural killer cell derived conditions. Accordingly, the scope of protection is not limited by the description set out above, but is only limited by the claims which follow, that scope including all equivalents of the subject matter of the claims. All patents, patent applications and publications cited herein are hereby incorporated herein by reference to the extent that they provide materials, methods and explanatory details supplementary to those set forth herein. The discussion of certain references in the Description of Related Art, above, is not an admission that they are prior art to the present invention.

What is claimed is:

1. An in vitro method of suppressing Janus tyrosine kinase 3 (Jak3)-dependent proliferation of a cell expressing Janus tyrosine kinase 3, comprising:
    selectively targeting Jak3 activity in the cell for inhibition by contacting the cell with at least one compound of the formula (I)

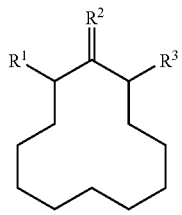

wherein
    $R_1$ is H, =$CH_2$, $CH_2N(CH_3)_2$, $CH_2SC(O)CH_3$, $CH_2SC_6H_5$, $CH_2SCH_2$-(4-$C_6H_4OCH_3$), $CH_2SC(O)C_6H_5$ or $CH_2N(CH_2CH_3)_2$;
    $R^2$ is O;
    $R^3$ is $CH_2N(CH_3)_2$, $CH_2N(CH_2CH_3)_2$ or $CH_2$—(N-morphyl);
or a salt thereof, at a concentration effective to selectively inhibit Janus tyrosine kinase 3 activity, whereby Jak3-dependent proliferation of the cell is suppressed.

2. The method of claim 1 wherein $R^1$ is $CH_2N(CH_3)_2$ and $R^3$ is $CH_2N(CH_3)_2$.

3. The method of claim 2 wherein said compound is the meso stereoisomer.

4. The method of claim 1 wherein the cell is of lymphoid or myeloid origin.

5. The method of claim 1 wherein selectively inhibiting Jak3 activity interferes with the signal 3 pathway, such that cell division is blocked.

6. The method of claim 1 wherein, at said concentration effective to selectively inhibit said Janus tyrosine kinase 3, said at least one compound is non-inhibitory or is less inhibitory of protein tyrosine kinase activity other than Janus tyrosine kinase 3 activity.

7. The method of claim 1 wherein said cell is a T-cell expressing Jak3 and Janus tyrosine kinase 2 (Jak2), and the method comprises inhibiting Jak3 activity at least 3 fold more than inhibiting Jak2 activity in said T-cells.

8. The method of claim 1 comprising choosing at least one said compound which is less capable of inhibiting Jak2 and Stat5a/b activation by prolactin (PRL) at a concentration sufficient to inhibit Jak3 and Stat5a/b activated by IL2.

9. The method of claim 4 wherein said cell is selected from the group consisting of T-cells, B-cells, natural killer (NK) cells and monocytes.

10. The method of claim 1 wherein $R^1$ is H.

11. The method of claim 1 wherein $R^1$ is =$CH_2$.

12. The method of claim 1 wherein $R^1$ is $CH_2N(CH_3)_2$.

13. The method of claim 1 wherein $R^1$ is $CH_2SC(O)CH_3$.

14. The method of claim 1 wherein $R^1$ is $CH_2SC_6H_5$.

15. The method of claim 1 wherein $R^1$ is $CH_2SCH_2$-(4-$C_6H_4OCH_3$).

16. The method of claim 1 wherein $R^1$ is $CH_2SC(O)C_6H_5$.

17. The method of claim 1 wherein $R^1$ is $CH_2N(CH_2CH_3)_2$.

18. The method of claim 1 wherein $R^3$ is $CH_2N(CH_3)_2$.

19. The method of claim 1 wherein $R^3$ is $CH_2N(CH_2CH_3)_2$.

20. The method of claim 1 wherein $R^3$ is $CH_2$-(N-morphyl).

21. An in vitro method of suppressing undesired Janus tyrosine kinase 3-dependent proliferation of a cell expressing Janus tyrosine kinase 3, comprising:
    selectively targeting Janus tyrosine kinase 3 activity in the cell for inhibition by contacting the cell with a compound of the formula

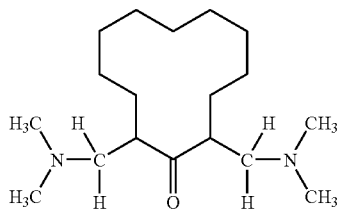

or a salt thereof, at a concentration effective to selectively inhibit the activity of said Janus tyrosine kinase 3 and thereby suppressing undesired Janus tyrosine kinase 3-dependent proliferation of said cell.

22. An in vivo method of suppressing an undesired Jak3-dependent function of a cell expressing Janus tyrosine kinase 3 (Jak3) in a mammalian allograft recipient, comprising:
   administering to said allograft recipient a therapeutically effective amount of a pharmaceutical composition containing at least one compound of the formula (I)

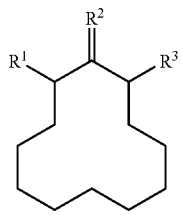

wherein
$R^1$ is H, $=CH_2$, $CH_2N(CH_3)_2$, $CH_2SC(O)CH_3$, $CH_2SC_6H_5$, $CH_2SCH_2$-(4-$C_6H_4OCH_3$), $CH_2SC(O)C_6H_5$ or $CH_2N(CH_2CH_3)_2$;
$R^2$ is O;
$R^3$ is $CH_2N(CH_3)_2$, $CH_2N(CH_2CH_3)_2$ or $CH_2$-(N-morphyl),
or pharmaceutically acceptable salt thereof, in a pharmaceutically acceptable carrier, to suppress proliferation of a cell expressing Jak3 in said recipient to treat allograft rejection in said recipient.

23. The method of claim 22 wherein said cell is a T-cell and said amount of said pharmaceutical composition is effective to block cell division in said T-cell.

24. The method of claim 23 wherein said undesired function comprises a t-cell mediated immune response, and wherein blocking cell division in a plurality of said t-cells provides T-cell mediated immunosuppression in said allograft recipient.

25. The method of claim 22 comprising continuously administering said pharmaceutical composition to the allograft recipient.

26. The method of claim 22 comprising periodically administering said pharmaceutical composition to the allograft recipient.

27. The method of claim 22 wherein suppression of said undesired Jak3-dependent cell function comprises interfering with the signal 3 pathway in the cell.

28. The method of claim 22 wherein one said compound is represented by the formula

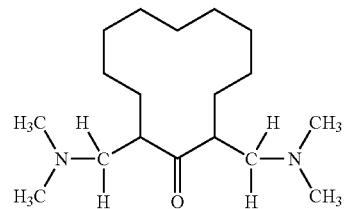

or a salt thereof.

29. The method of claim 22, wherein said administering of said composition enhances allograft survival in said mammalian allograft recipient.

30. The method of claim 22 wherein $R^1$ is H.
31. The method of claim 22 wherein $R^1$ is $=CH_2$.
32. The method of claim 22 wherein $R^1$ is $CH_2N(CH_3)_2$.
33. The method of claim 22 wherein $R^1$ is $CH_2SC(O)CH_3$.
34. The method of claim 22 wherein $R^1$ is $CH_2SC_6H_5$.
35. The method of claim 22 wherein $R^1$ is $CH_2SCH_2$-(4-$C_6H_4OCH_3$).
36. The method of claim 22 wherein $R^1$ is $CH_2SC(O)C_6H_5$.
37. The method of claim 22 wherein $R^1$ is $CH_2N(CH_2CH_3)_2$.
38. The method of claim 22 wherein $R^3$ is $CH_2N(CH_3)_2$.
39. The method of claim 22 wherein $R^3$ is $CH_2N(CH_2CH_3)_2$.
40. The method of claim 22 wherein $R^3$ is $CH_2$-(N-morphyl).

* * * * *